US006762336B1

(12) United States Patent
MacPhee et al.

(10) Patent No.: US 6,762,336 B1
(45) Date of Patent: Jul. 13, 2004

(54) HEMOSTATIC SANDWICH BANDAGE

(75) Inventors: Martin J. MacPhee, Montgomery Village, CA (US); William H. Drohan, Springfield, VA (US); Dawson Beall, Gaithersburg, MD (US); Stanley A. Friedman, Bartonsville, MD (US); David Tuthill, Frederick, MD (US); Valdislav Bayer, Gaithersburg, MD (US)

(73) Assignee: The American National Red Cross, Rockville, MD (US)

( * ) Notice: Subject to any disclaimer, the term of this patent is extended or adjusted under 35 U.S.C. 154(b) by 0 days.

(21) Appl. No.: 09/890,795

(22) PCT Filed: May 19, 1999

(86) PCT No.: PCT/US99/10952

§ 371 (c)(1),
(2), (4) Date: Mar. 22, 2002

(87) PCT Pub. No.: WO99/59647

PCT Pub. Date: Nov. 25, 1999

Related U.S. Application Data

(60) Provisional application No. 60/085,931, filed on May 19, 1998.

(51) Int. Cl.[7] .............................................. A61F 13/00
(52) U.S. Cl. .......................... 602/48; 602/42; 602/43
(58) Field of Search ............. 602/41–59; 604/304–308; 424/422, 423, 426, 443–449

(56) References Cited

U.S. PATENT DOCUMENTS

| | | | |
|---|---|---|---|
| 2,533,004 A | 12/1950 | Ferry et al. .................. 260/112 |
| 3,089,815 A | 5/1963 | Lieb et al. ...................... 167/58 |
| 3,523,807 A | 8/1970 | Gerendas .................... 106/124 |
| 3,723,244 A | 3/1973 | Breillatt, Jr. ................. 162/151 |
| 4,265,233 A | 5/1981 | Sugitachi et al. ........... 128/156 |
| 4,298,598 A | 11/1981 | Schwarz et al. ............. 424/101 |
| 4,321,711 A | 3/1982 | Mano .............................. 3/1.4 |
| 4,359,049 A | 11/1982 | Redl et al. ............. 128/218 PA |
| 4,362,567 A | 12/1982 | Schwarz et al. ............. 106/157 |
| 4,373,519 A | 2/1983 | Errede et al. ................ 128/156 |
| 4,377,159 A | 3/1983 | Hansen ........................ 128/155 |
| 4,377,572 A | 3/1983 | Schwarz et al. ............. 424/101 |
| 4,393,041 A | 7/1983 | Brown et al. .................. 424/21 |
| 4,394,370 A | 7/1983 | Jefferies ....................... 424/15 |
| 4,407,787 A | 10/1983 | Stemberger .................. 424/28 |
| 4,414,976 A | 11/1983 | Schwarz et al. ........ 128/334 R |
| 4,427,650 A | 1/1984 | Stroetmann .................. 424/46 |
| 4,427,651 A | 1/1984 | Stroetmann .................. 424/46 |
| 4,442,655 A | 4/1984 | Stroetmann .................. 53/428 |
| 4,453,939 A | 6/1984 | Zimmerman et al. ....... 604/368 |
| 4,472,840 A | 9/1984 | Jefferies .......................... 3/1.9 |
| 4,516,276 A | 5/1985 | Mittelmeier et al. .......... 3/1.91 |
| 4,548,763 A | 10/1985 | Nalewajek et al. ......... 260/989 |
| 4,597,960 A | 7/1986 | Cohen ......................... 424/28 |
| 4,600,574 A | 7/1986 | Lindner et al. ............... 424/28 |
| 4,606,337 A | 8/1986 | Zimmermann et al. ..... 128/156 |
| 4,617,293 A | 10/1986 | Wahlig et al. ................. 514/41 |
| 4,619,913 A | 10/1986 | Luck et al. ...................... 514/2 |
| 4,619,989 A | 10/1986 | Urist ........................... 530/417 |
| 4,627,879 A | 12/1986 | Rose et al. .................. 106/124 |

(List continued on next page.)

FOREIGN PATENT DOCUMENTS

| | | |
|---|---|---|
| AU | B-83581/82 | 11/1982 |
| AU | B-43122/85 | 12/1985 |
| AU | B-75097/87 | 1/1988 |
| CA | 1119516 | 3/1982 |
| CA | 1 168 982 | 6/1984 |
| EP | 0 081 990 A1 | 11/1987 |
| EP | 0 312 208 A1 | 4/1989 |
| EP | 0 443 724 A1 | 8/1991 |
| EP | 0 485 210 A2 | 5/1992 |
| EP | 0 562 864 A1 | 9/1993 |
| GB | 2 041 942 A | 9/1980 |
| GB | 1 584 080 | 2/1981 |
| GB | 2 042 556 A | 9/1982 |
| GB | 2 102 811 A | 2/1983 |
| GB | 2 137 209 A | 10/1984 |
| GB | 2 185 747 A | 7/1987 |
| JP | 60-204725 | 10/1985 |
| WO | WO 81/00516 A1 | 3/1981 |
| WO | WO 86/00526 A1 | 1/1986 |
| WO | WO 86/01814 | 3/1986 |

(List continued on next page.)

OTHER PUBLICATIONS

Holcomb, J.B. et al., "Implications of New Dry Fibrin Sealant Technology for Trauma Surgery," *Damage Control Surg.* 77:943–952, W.B. Saunders, Inc. (1997).

Dialog File 351, Accession No. 3793917, Derwent WPI English language abstract for EP 0 090 997 A2 (Document AL1).

International Search Report for International Application No. PCT/US99/10952, mailed Sep. 17, 1999.

Achauer, B.M., et al., "The Hemostatic Effect of Fibrin Glue on Graft Donor Sites," *J. Burn. Care Rehabil.* 15:24–28, Burn Science Publishers, Inc. (1994).

Adelmann–Grill, B.C., et al., "Chemotactic migration of normal dermal fibroblasts towards epidermal growth factor and its modulation by platelet–derived growth factor and transforming growth factor–beta," *Eur. J. Cell. Biol.* 51:322–326, Wissenschaftliche Verlagsgesellschaft mbH (1990).

(List continued on next page.)

*Primary Examiner*—Kim M. Lewis
(74) *Attorney, Agent, or Firm*—Sterne, Kessler, Goldstein & Fox P.L.L.C.

(57) ABSTRACT

The present invention relates to a haemostatic multilayer bandage that comprises preferably a thrombin layer between two fibrinogen layers. The dressing may contain other resorbable materials such as glycolic acid or lactic acid based polymers or copolymers. The inventive haemostatic bandage is useful for the treatment of wounded tissue.

9 Claims, No Drawings

U.S. PATENT DOCUMENTS

| | | | |
|---|---|---|---|
| 4,631,055 A | 12/1986 | Redl et al. | 604/82 |
| 4,642,120 A | 2/1987 | Nevo et al. | 623/16 |
| 4,714,457 A | 12/1987 | Alterbaum | 494/37 |
| 4,717,717 A | 1/1988 | Finkenaur | 514/21 |
| 4,761,471 A | 8/1988 | Urist | 530/350 |
| 4,789,732 A | 12/1988 | Urist | 530/350 |
| 4,816,339 A | 3/1989 | Tu et al. | 428/421 |
| 4,820,626 A | 4/1989 | Williams et al. | 435/1 |
| 4,837,379 A | 6/1989 | Weinberg | 424/101 |
| 4,861,757 A | 8/1989 | Antoniades et al. | 514/21 |
| 4,874,746 A | 10/1989 | Antoniades et al. | 514/21 |
| 4,909,251 A | 3/1990 | Seelich | 606/213 |
| 4,928,603 A | 5/1990 | Rose et al. | 106/124 |
| 4,952,403 A | 8/1990 | Vallee et al. | 424/422 |
| RE33,375 E | 10/1990 | Luck et al. | 514/2 |
| 4,969,880 A | 11/1990 | Zamierowski | 604/305 |
| 4,983,581 A | 1/1991 | Antoniades et al. | 514/12 |
| 4,997,425 A | 3/1991 | Shioya et al. | 604/304 |
| 5,019,559 A | 5/1991 | Antoniades et al. | 514/21 |
| 5,023,082 A | 6/1991 | Friedman et al. | 424/426 |
| 5,024,742 A | 6/1991 | Nesburn et al. | 204/157.68 |
| 5,030,215 A | 7/1991 | Morse et al. | 604/410 |
| 5,034,375 A | 7/1991 | Antoniades et al. | 514/12 |
| 5,035,887 A | 7/1991 | Antoniades et al. | 424/85.2 |
| 5,059,123 A | 10/1991 | Jernberg | 433/215 |
| 5,100,396 A | 3/1992 | Zamierowski | 604/305 |
| 5,124,155 A | 6/1992 | Reich | 424/428 |
| 5,139,527 A | 8/1992 | Redl et al. | 623/66 |
| 5,171,318 A | 12/1992 | Gibson et al. | 623/5 |
| 5,171,579 A | 12/1992 | Ron et al. | 424/486 |
| 5,206,023 A | 4/1993 | Hunziker | 424/423 |
| 5,219,328 A | 6/1993 | Morse et al. | 604/49 |
| 5,226,877 A | 7/1993 | Epstein | 604/35 |
| 5,290,552 A | 3/1994 | Sierra et al. | 424/94.64 |
| 5,294,314 A | 3/1994 | Nesburn et al. | 204/157.68 |
| 5,368,858 A | 11/1994 | Hunziker | 424/423 |
| 5,431,790 A | 7/1995 | Nesburn et al. | 204/157.68 |
| 5,702,715 A | 12/1997 | Nikolaychik et al. | 424/402 |
| 5,723,010 A * | 3/1998 | Yui et al. | 623/15 |
| 5,763,411 A | 6/1998 | Edwardson et al. | 514/21 |
| 6,054,122 A | 4/2000 | MacPhee et al. | 424/94.4 |
| 6,117,425 A | 9/2000 | MacPhee et al. | 424/94.64 |
| 6,124,273 A | 9/2000 | Drohan et al. | 514/55 |
| 6,197,325 B1 | 3/2001 | MacPhee et al. | 424/426 |

FOREIGN PATENT DOCUMENTS

| | | |
|---|---|---|
| WO | WO 86/03122 A1 | 6/1986 |
| WO | WO 91/09573 A1 | 7/1991 |
| WO | WO 91/17744 A1 | 11/1991 |
| WO | WO 92/09301 A1 | 6/1992 |
| WO | WO 92/09697 A1 | 6/1992 |
| WO | WO 92/13565 A1 | 8/1992 |
| WO | WO 92/22312 A1 | 12/1992 |
| WO | WO 93/05067 A1 | 3/1993 |
| WO | WO 94/20133 | 9/1994 |
| WO | WO 97/28832 | 8/1997 |

OTHER PUBLICATIONS

Akrami, R., et al., "Replacement of the Thoraric Aorta by Sealed Dacron Prostheses," *Thoraxchirurgie* 26:144–147, Georg Thieme Verlag Stuttgart (1978) Summary Only.

Albrektsson, T., et al., "Fibrin Adhesive System (FAS) Influence on Bone Healing Rate," *Acta orthop. scand.* 53:757–763, Munksgaard (1982).

Alving, B.M., et al., "Fibrin sealant: summary of a conference on characteristics and clinical uses," *Transfusion* 35:783–790, The American Association of Blood Banks (1995).

Allen, B.T., et al., "Influence of endothelial cell seeding on platelet deposition and patency in small-diameter Dacron arterial grafts," *J. Vasc. Surg.* 1:224–233, Mosby–Year Book Inc. (1984).

The American Red Cross, "Growth Factor–Supplemented Fibrin Glue," in *The American Red Cross Biomedical Research and Development Report*, p. 21, The American Red Cross (1989).

The American Red Cross, "Growth Factor–Supplemented Fibrin Glue," in *The American Red Cross Biomedical Research and Development Report*, p. 20, The American Red Cross (1990).

Andreassen, T.T., and Jorgensen, P.H., "Biomechanical Properties and Collagen Formation in Subcutaneously Implanted Cellulose Sponges Treated with Fibrin Sealant," *Eur. surg. Res.* 17:264–268, S.Karger AG (1985).

Arbes, H., et al., "First Clinical Experience with Heterologous Cancellous Bone Grafting Combined with the Fibrin Adhesive System (F.A.S.)," *Arch. Orthop. Traumat. Surg.* 98:183–188, J.F.Bergmann Verlag (1981).

Bagdy, D., et al., "Application of Bovine Fibrin Foam and of a Mixture of Thrombin and Fibrin Powders as Haemostatic Agents," *Acta. Physiol. Acad. Sci. Hung.* 2:493–504, Magyar Tudományos Akadémia (1951).

Bailey, O.T., and Ingraham, F.D., "Chemical, Clinical, and Immunological Studies on the Products of Human Plasma Fractionation. XXI. The Use of Fibrin Foam as Hemostatic Agent in Neurosurgery: Clinical and Pathological Studies," *J. Clin. Invest.* 23:591–596, The American Society for Clinical Investigation (1944).

Bailey, O.T., and Ingraham, F.D., "Chemical, Clinical, and Immunological Studies on the Products of Human Plasma Fractionation. XXII. Fibrin Films in Neurosurgery, with Special Reference to Their Use in the Repair of Dural Defects and in the Prevention of Meningocerebral Adhesions," *J. Clin. Invest.* 23:597–600, The American Society for Clinical Investigation (1944).

Bailey, O.T., et al., "Fibrin Film in Neurosurgery, Further Studies: The Insertion of Fibrin Film Between the Sutured Dura and The Intact Leptomeninges; The Effect of Roentgen Therapy on Tissue Reactions to Fibrin Film," *J. Neurosurg.* 4:465–471, American Association of Neurosurgical Surgeons (1947).

Baird, A., and Walicke, P.A., "Fibroblast growth factors," *Brit. Med. Bull.* 45:438–452, The British Council (1989).

Berger, K., et al., "Healing of Arterial Prostheses in Man: Its Incompleteness," *Ann. Surg.* 175:118–127, J.B. Lippincott Company (1972).

Bishara, S.E., et al., "Effects of a Fibrin–Sealant Wound Dressing on the Healing of Full–Thickness Wounds of the Hard Palate: Preliminary Report," *Cleft Palate J.* 23:144–152, Allen Press Inc. (1986).

Bösch, P., et al., "The Technic of Fibrin Glue in Cancellous Bone Transplants," *Arch. orthop. Unfall–Chir.* 90:63–75, J.F. Bergmann–Verlag (1977) Summary Only.

Bösch, P., et al., "Autologous Cancellous Bone Grafting in Rabbits Using a Fibrinogen Adhesive System," *Wiener klinische Wochenschrift* 91:628–634, Springer–Verlag Wien (1979) Summary Only.

Bösch, P., "Experimental Investigations of the Effect of the Fibrin Adhesive on the Kiel Heterologous Bone Graft," *Arch. Orthop. Traumat. Surg.* 96:177–185, J.F. Bergmann Verlag (1980).

Bösch, P., "Bone Grafting with Fibrin–Glue," *Weiner klinische Wochenschrift* 93:3–26, Springer–Verlag Wien (1981).

Borst, H.G., et al., "Fibrin adhesive: An important hemostatic adjunct in cardiovascular operations," *J. Thorac. Cardiovasc. Surg.* 84:548–553, The C.V. Mosby Co. (1982).

Brown, D.M,. et al., "Decreased Wound Contraction With Fibrin Glue–Treated Skin Grafts," *Arch. Surg.* 127:404–406, American Medical Association (1992).

Burgess, W.H., and Maciag, T., "The Heparin–Binding (Fibroblast) Growth Factor Family of Proteins," *Annu. Rev. Biochem.* 58:575–606, Annual Reviews Inc. (1989).

Byrne, D.J., et al., "Effect of fibrin glues on the mechanical properties of healing wounds," *Br. J. Surg.* 78:841–843, Butterworth–Heinemann Ltd. (1991).

Carter, D.M., et al., "Clinical Experience with Crude Preparations of Growth Factors in Healing of Chronic Wounds in Human Subjects," *Growth Factors and Other Aspects of Wound Healing: Biological and Clinical Implications*, Alan R. Liss, Inc., pp. 303–317 (1988).

Clark, A.M., et al., "Fixation of Skin–Grafts with Human Plasma and Thrombin," *Lancet* 1:498–500, The Lancet Ltd. (1945).

Clowes, A.W., and Kohler, T., "Graft Endothelialization: The Role of Angiogenic Mechanisms," *J. Vasc. Surg.* 13:734–736, Mosby–Year Book, Inc. (1991).

Clowes, A.W., et al., "Mechanisms of Arterial Graft Healing. Rapid Transmural Capillary Ingrowth Provides a Source of Intimal Endothelium and Smooth Muscle in Porous PTFE Prostheses," *Am. J. Pathol.* 123:220–230, American Society of Investigative Pathology (1986).

Conant, M., et al., "Treatment of Condylomata Acuminata with Intralesional 5–Fluorouracil Therapeutic Implant (MPI 5003)," *Clinical Res.* 39:818A, The American Federation for Clinical Research (1991).

Cronkite, E.P., et al., "Use of Thrombin and Fibrinogen in Skin Grafting: Preliminary Report," *J.A.M.A.* 124:976–978, The American Medical Association (1944).

Cziperle, D., et al., "Enhanced Endothelialization of Expanded Polytetrafluoroethylene Grafts by Heparin Binding Growth Factor–Type I (HBGF–1) Pretreatment," Presented at the Society of University Surgeons (Feb. 1992).

Davidson, J., et al., "Mechanisms of Accelerated Wound Repair Using Epidermal Growth Factor and Basic Fibroblast Growth Factor," in *Growth Factors and Other Aspects of Wound Healing: Biological and Clinical Implications*, Alan R. Liss, Inc., pp. 63–75 (1988).

Dees, J.E., "The Use of an Intrapelvic Coagulum in Pyelolithotomy: Preliminary Report," *South. Med. J.* 36:167–175, The Southern Medical Association (1943).

Dees, J.E., and Fox, H., "The Properties of Human Fibrinogen Coagulum–Preliminary Report," *J. Urol.* 49:503–511, The Williams & Wilkins Company (1943).

Dees, J.E., "Chemical, Clinical, and Immunological Studies on the Products of Human Plasma Fractionation. XVIII. Fibrinogen Coagulum as an Aid in the Operative Removal of Renal Calculi," *J. Clin. Invest.* 23:576–579, The American Society for Clinical Investigation (1944).

Dees, J.E., "The Use of a Fibrinogen Coagulum in Pyelolithotomy," *J. Urol.* 56:271–283, The Williams & Wilkins Company (1946).

Deyerling, W., et al., "A Suspension of Fibrin Glue and Antibiotic for Local Treatment of Myocotic Aneurysms in Endocarditis—An Experimental Study," *Thorac. cardiovasc. Surgeon* 32:369–372, Georg Thieme Verlag Stuttgart (1984).

Dresdale, A., et al., "Hemostatic Effectiveness of Fibrin Glue Derived from Single–Donor Fresh Frozen Plasma," *Ann. Thorac. Surg.* 40:385–387, The Society of Thoracic Surgeons (1985).

Berguer, R., et al., "Warning: Fatal Reaction to the Use of Fibrin Glue in Deep Hepatic Wounds. Case Reports," *J. Trauma* 31:408–411, Williams & Wilkens Company (1991).

de la Garza, J.L., and Rumsey Jr., E., "Fibrin Glue and Hemostatis in Liver Trauma: A Case Report," *J. Trauma* 30:512–513, Williams & Wilkens Company (1990).

Jakob, H., et al., "Use of fibrin sealant for reinforcing arterial anastomoses," *J. Vasc. Surg.* 1:171–180, C.V. Mosby Company (1984).

Kendrick, D.B., et al., "Plasma Fractionation," in *Blood Program in World War II*, Coates, Jr., J.B., and McFetridge, E.M., eds., Office of the Surgeon General, Dept. of the Army, Washington, D.C. pp. 363–369 (1964).

Kram, H.B., et al., "Techniques of Splenic Preservation Using Fibrin Glue," *J. Trauma* 30:97–101, Williams & Wilkens Company (1990).

Ochsner, M.G., et al., "Fibrin Glue as a Hemostatic Agent in Hepatic and Splenic Trauma," *J. Trauma* 30:884–887, Williams & Wilkens Company (1990).

Matthew, T.L., et al., "Four Years Experience With Fibrin Sealant in Thoracic and Cardiovascular Surgery," *Ann. Thorac. Surg.* 50:40–44, Elsevier (1990).

Ness, P.M., and Perkins, H.A., "Cryoprecipitate as a Reliable Source of Fibrinogen Replacement," *JAMA* 241:1690–1691, American Medical Association (1979).

Rapaport, S.I., "Clinical Significance of Antibodies to Bovine and Human Thrombin and Factor V After Surgical Use of Bovine Thrombin," *Am. J. Clin. Pathol.* 97:84–91, J.B. Lippincott Company (1992).

Reiss, R.F., and Oz, M.C., "Autologous Fibrin Glue: Production and Clinical Use," *Transfus. Med. Rev.* 10:85–92, W.B. Saunders Company (1996).

Rocko, J.M., et al., "A.A.S.T. Abstracts: Exsanguination in public—a preventable death," *J. Trauma* 22:635, Williams & Wilkens Company (1982).

Schiele, U., et al., "Haemostyptic Preparations on the Basis of Collagen alone and as fixed Combination with Fibrin Glue," *Clin. Mater.* 9:169–177, Elsevier Science Publishers, Ltd. (1992).

Sloand, E.M., et al., "Safety of the Blood Supply," *JAMA* 274:1368–1373, American Medical Association (1995).

Spotnitz, W.D., "Fibrin Sealant in the United States: Clinical Use at the University of Virginia," *Thromb. Haemost.* 74:482–485, Stuttgart F.K. Schattauer Verlag (1995).

Zimmerman, L.M., and Veith, I., "Celsus and the Alexandrians," in *Great Ideas in the History of Surgery*, Zimmerman, L.M., and Veith, I., eds., Norman Publishing, San Francisco, CA, p. 31 (1993).

Dresdale, A., et al., "Preparation of fibrin glue from single–donor fresh–frozen plasma," *Surgery* 97:750–755, Mosby–Year Book, Inc. (1985).

Durham, L.H., et al., "A method for preparation of fibrin glue," *J. Laryngol. Otol.* 101:1182–1186, Headley Brothers Ltd. (1987).

Dvorak, H.F., et al., "Fibrin Containing Gels Induce Angiogenesis. Implications for Tumor Stroma Generation and Wound Healing," *Lab. Invest.* 57:673–686, The United States and Canadian Academy of Pathology, Inc. (1987).

Epstein, G.H., et al., "A New Autologous Fibrinogen–Based Adhesive for Otologic Surgery," *Ann. Otol. Rhinol. Laryngol.* 95:40–45, Annals Publishing Company (1986).

Ferry, J.D., and Morrison, P.R., "Chemical, Clinical, and Immunological Studies on the Products of Human Plasma Fractionation. XVI. Fibrin Clots, Fibrin Films, and Fibrinogen Plastics," *J. Clin. Invest.* 23:566–572, The American Society for Clinical Investigation (1944).

Foxall, T.L., et al., "Adult Human Endothelial Cell Coverage of Small–Caliber Dacron and Polytetrafluoroethylene Vascular Protheses in Vitro," *J. Surg. Res.* 41:158–172, Academic Press, Inc. (1986).

Froesch, R.R., et al., "Actions of Insulin–Like Growth Factors," *Ann. Rev. Physiol.* 47:443–467, Annual Reviews, Inc. (1985).

Frucht–Perry, J., et al., "Fibrin–Enmeshed Tobramycin Liposomes: Single Application Topical Therapy of Pseudonas Keratitis," *Cornea* 11:393–397, Raven Press, Ltd. (1992).

Gerendás, M., "Fibrin Products as Aids in Hemostatis and Wound Healing," in *Fibrinogen*, Chapter 13, Laki, K., Ed., Marcel Dekker, New York, pp. 277–316 (1968).

Gersdorff, M.C.H., and Robillard, T.A.J., "'How I do It'— Otology and Neurotology. A Specific Issue and Its Solution. A New Procedure for Bone Reconstruction in Oto–Microsurgery: A Mixture of Bone Dust And Fibrinogen Adhesive," *Laryngoscope* 95:1278–1280, The Laryngoscope Company (1985).

Gibble, J.W., and Ness, P.M., "Fibrin glue: the perfect operative sealant?," *Transfusion* 30:741–747, American Association of Blood Banks (1990).

Glynn, J.H., and Richardson, J.H., "The Antigenic Properties of Fibrin Films and Foams Prepared from Human and from Bovine Blood Plasma," *J. Immunol.* 53:143–150, The Williams & Wilkens Company (1946).

Gospodarowicz, D., et al., "Structural Characterization and Biological Functions of Fibroblast Growth Factor," *Endocr. Rev.* 8:95–114, The Endocrine Society (1987).

Goudarzi, Y.M., "Clinical Experiences with a Fibrin–Nebacetin Bone Marrow Combination in the Treatment of Chronic Bone Infections and as Local Infection Prophylaxis in Non–Infected Bone Diseases," *Akt. Traumatol.* 13:205–209, Georg Thieme Verlag Stuttgart (1983) Summary Only.

Graham, L.M., et al., "Expanded polytetrafluoroethylene vascular protheses seeded with enzymatically derived and cultured canine endothelial cells," *Surgery* 91:550–559, The C.V. Mosby Co. (1982).

Greco, F., et al., "Fibrin–antibiotic mixtures: An in vitro study assessing the possibility of using a biologic carrier for local drug delivery," *J. Biomed. Mater. Res.* 25:39–51, John Wiley & Sons, Inc. (1991).

Greenhalgh, D.G., et al., "PDGF and FGF Stimulate Wound Healing in the Genetically Diabetic Mouse," *Am. J. Path.* 136:1235–1246, American Association of Pathologists (1990).

Greisler, H.P., et al., "Endothelial Cell Growth Factor Attachment to Biomaterials," *Trans. Am. Soc. Artif. Intern. Organs* 32:346–349, American Society for Artificial Internal Organs (1986).

Greisler, H.P., et al., "Biomaterial pretreatment with ECGF to augment endothelial cell proliferation," *J. Vasc. Surg.* 5:393–399 and 402, Mosby–Year Book, Inc. (1987).

Greisler, H.P., et al., "Enhanced endothelialization of expanded polytetrafluoroethylene grafts by fibroblast growth factor type 1 pretreatment," *Surgery* 112:244–255, Mosby–Year Book, Inc. (1992).

Greisler, H.P., et al., "Enhancement of Polytetrafluoroethylene Endothelialization by Pretreatment with Fibrin Glue Containing Heparin Binding Growth Factor–Type I (HBGF–1)," presented at the Proceedings of the Cardiovascular Science and Technology Conference, p. 50 (Dec. 2–4, 1991).

Gundry, S.R., and Behrendt, D.M., "A Quantitative and Qualitative Comparison of Fibrin Glue, Albumin, and Blood as Agents to Pretreat Porous Vascular Grafts," *J. Surg. Res.* 43:75–77, Academic Press, Inc. (1987).

Harker, L.A., et al., "Platelet Consumption by Arterial Prostheses: The Effects of Endothelization and Pharmacologic Inhibition of Platelet Function," *Ann. Surg.* 186:594–601, Lippincott Williams & Wilkins (1977).

Harris, H.I., "Heterogenous Skin Grafts by Coagulum Contact Method," *Am. J. Surg.* 65:315–320, The American Journal of Surgery, Inc. (1944).

Harrison, J.H., and Trichel, B. E., "Experiences with Fibrin Coagulum in Pyelolithotomy," *j. Urol.* 62:1–12, The Williams & Wilkins Company (1949).

Harrison, E.T., et al., "Osteogenin Promotes Reexpression of Cartilage Phenotype by Dedifferentiated Articular Chondrocytes in Serum–Free Medium," *Exp. Cell Res.* 192:340–345, Academic Press, Inc. (1991).

Härting, F., et al., "Glued Fixation of Split–Skin Graft to the Bony Orbit Following Exenteration," *Plas. Reconstruc. Surg.* 76:633–635, Lippincott Williams & Wilkins (1985).

Hattori, T., "Experimental Investigations of Osteogenesis and Chondrogenesis by Implant of BMP–Fibrin Glue Mixture," *J. Jpn. Orthop. Assoc.* 64:824–834, Japanese Orthopedic Association (1990) Summary and Figures Only.

Haverich, A., et al., "The Use of Fibrin Glue for Sealing Vascular Protheses of High Porosity," *Thorac. cardiovasc. Surgeon* 29:252–254, Georg Thieme Verlag Stuttgart (1981).

Haverich, A., et al., "Evaluation of Fibrin Seal in Animal Experiments," *Thorac. cardiovasc. Surgeion* 30:215–222, Georg Thieme Verlag Stuttgart (1982).

Haverich, A., et al., "Histopathological Evaluation of Woven and Knitted Dacron Grafts for Right Ventricular Conduits: A Comparative Experimental Study," *Ann. Thorac. Surg.* 37:404–411, Elsevier Science Inc. (1984).

Haverich, A., et al., "Pericardial Flap–Plasty for Protection of the Tracheal Anastomosis in Heart–Lung Transplantation," *J. Card. Surg.* 4:136–139, Futura Publishing Company, Inc (1989).

Haverich, A., et al., "Prevention of graft infection by bonding of gentamycin to Dacron prostheses," *J. Vasc. Surg.* 15:187–193, Mosby–Year Book, Inc. (1992).

Hawn, C.v.Z, et al., "Chemical, Clinical and Immunological Studies on the Products of Human Plasma Fractionation. XIX. A Note on the Use of Fibrinogen and Thrombin in the Surface Treatment of Burns," *J. Clin. Invest.* 23:580–585, The American Society for Clinical Investigation (1944).

Hayek, A., et al., "An in Vivo Model for Study of the Angiogenic Effects of Basic Fibroblast Growth Factor," *Biochem. Biophys. Res. Commun.* 147:876–880, Academic Press, Inc. (1987).

Herring, M.B., et al., "Endothelial Seeding of Polytetrafluoroethylene Popliteal bypasses," *J. Vasc. Surg. 6*:114–118, Mosby–Year Book, Inc. (1987).

Ho, H.–O., et al., "Drug Release From Glutaraldehyde–Treated Fibrin Gels," *Drug Des. Del. 7*:65–73, Harwood Academic Publishers GmbH (1990).

Hoffman, H.A., "Coagulum Pyelolithotomy," *Am. J. Surg. 79*:598–602, Excerpta Medica, Inc. (1950).

Holcomb, J.B., et al., "Implications of New Dry Fibrin Sealant Technology for Trauma Surgery," *Surg. Clin. North Am. 77*:943–952, W.B. Saunders Company (Aug. 1997).

Ikossi–O'Connor, M.G., et al., "The Role of Fibrin Adhesive in Vascular Surgery," *J. Surg. Oncol. 23*:151–152, Alan R. Liss, Inc. (1983).

Ingraham, F.D., and Bailey, O.T., "Clinical Use of Products of Human Plasma Fractionation. III. The Use of Products of Fibrinogen and Thrombin in Surgery," *J.A.M.A. 126*:680–685, The American Medical Association (1944).

Ingraham, F.D., and Bailey, O.T., "The Use of Products Prepared from Human Fibrinogen and Human Thrombin in Neurosurgery. Fibrin Foams as Hemostatic Agents; Fibrin Films in Repair of Dural Defects and in Prevention of Meningocerebral Adhesions," *J. Neurosurg. 1*:23–39, Charles C. Thomas (1944).

Ingraham, F.D., et al., "The Use of Fibrin Film as Dural Substitute and in the Prevention of Meningocerebral Adhesions. Further Studies and Clinical Results," *J.A.M.A. 128*:1088–1091, The American Medical Association (1945).

István, L., et al., "Gastrointestinalis vérzések csillapítésa thrombin–fibrin készítménnyel," *Orv. Hetil. 105*:219–223, Markusovszky Lajos Foundation (1964).

Jarrell, B., et al., "Human adult endothelial cell growth in culture," *J. Vasc. Surg. 1*:757–764, Mosby–Year Book, Inc. (1984).

Jonas, R.A., et al., "Biological Sealants and Knitted Dacron: Porosity and Histological Comparisons of Vascular Graft Materials with and without Collagen and Fibrin Glue Pretreatments," *Ann. Thorac. Surg. 41*:657–663, Elsevier Science Inc. (1986).

Jonas, R.A., et al., "Biological Sealants and Knitted Dacron Conduits: Comparison of Collagen and Fibrin Glue Pretreatments in Circulatory Models," *Ann. Thorac. Surg. 44*:283–290, Elsevier Science Inc. (1987).

Kabuto, M., et al. "Experimental Study of Intraoperative Local Chemotherapy with Fibrin Glue Containing Nitosourea for Malignant Gliomas," *Surg. Neurol. 44*:151–157, Elsevier Science Inc. (1995).

Kaehler, J., et al., "Precoating substrate and surface configuration determine adherence and spreading of seeded endothelial cells on polytetrafluoroethylene grafts," *J. Vasc. Surg. 9*:535–541, The Society for Vascular Surgery and International Society for Cardiovascular Surgery, North American Chapter (1989).

Karck, M., et al., "Pretreatment of prosthetic valve sewing–ring with the antibiotic/fibrin sealant compound as a prophylactic tool against prosthetic valve endocarditis," *Eur. J. Cardio–thorac. Surg. 4*:142–146, Springer–Verlag (1990).

Kawamura, M., and Urist, M.R., "Human Fibrin Is a Physiologic Delivery System for Bone Morhogenetic Protein," *Clin. Orthop. 235*:302–310, Lippincott Williams & Wilkins (1988).

Kempczinski, R.F., et al., "Endothelial cell seeding of a new PTFE vascular prosthesis," *J. Vasc. Surg. 2*:424–429, Mosby–Year Book Inc. (1985).

Kesler, K.A., et al., "Enhanced strength of endothelial attachment on polyester elastomer and polytetrafluoroethylene graft surfaces with fibronectin substrate," *J. Vasc. Surg. 3*:58–64, Mosby–Year Book Inc. (1986).

Knighton, D.R., et al., "Classification and Treatment of Chronic Nonhealing Wounds," *Ann. Surg. 204*:322–330, Lippincott Williams & Wilkins (1986).

Knighton, D.R., et al., "The Use of Platelet Derived Wound Healing Formula in Human Clinical Trials," in *Growth Factors and Other Aspects of Wound Healing: Biological and Clinical Implications*, Alan R. Liss, Inc., pp. 319–329 (1988).

Knighton, D.R., et al., "Regulation of Cutaneous Wound Healing by Growth Factors," *Clin. Mater. 8*:229–241, Elsevier Science Publishers Ltd. (1991).

Knöbl, P.N., et al., "The protein C system in patients undergoing cardiopulmonary bypass," *J. Thorac. Cardiovasc. Surg. 94*:600–605, American Association for Thoracic Surgery (1987).

Kovács, B., and Kerényi, G., "Bioplast® fibrin coagulum in large cystic defects of the jaw," *Intl. J. Oral. Surg. 5*:111–116, Elsevier Science Inc. (1976).

Köveker, G., "Clinical Application of Fibrin Glue in Cardiovascular Surgery," *Thorac. cardiovasc. Surgeon 30*:228–229, Georg Thieme Verlag Stuttgart (1982).

Köveker, G., et al., "Clinical Experience with Fibrin Glue in Cardiac Surgery," *Thorac. cardiovasc. Surgeon 29*:287–289, Georg Thieme Verlag Stuttgart (1981).

Kóveker, G.B., et al., "Reduction of Thrombogenicity in Small–diameter Vascular Protheses Seeded with Autologous Endothelial Cells," *Thorac. cardiovasc. Surgeon 34*:49–51, Georg Thieme Verlag Stuttgart (1986).

Kram, H.B., et al., "Use of concentrated fibrinogen in experimental tracheal repair," *J. Biomed. Mater. Res. 20*:579–587, John Wiley & Sons, Inc. (1986).

Kram, H.B., et al., "Fibrin glue sealing of polytetrafluoroethylene vascular graft anastomoses: Comparison with oxidized cellulose," *J. Vasc. Surg. 8*:563–568, Mosby–Year Book, Inc. (1988).

Kram, H.B., et al., "Antibacterial Effects of Fibrin Glue–Antibiotic Mixtures," *J. Surg. Res. 50*:175–178, Academic Press, Inc. (1991).

Kratzat, R., et al., "Clinical Experiences with the Fibrin–Antibiotic Combination in Infections of the Bones and Soft Parts," *Akt. Chir. 17*:58–62, Georg Thieme Verlag Stuttgart (1982).

Kratzat, R., et al., "Erste klinische Erfahrungen mit dem Fibrin–Antibiotikim–Verbund bei der Osteomyelitis," *Orthop. Praxis 17*:852–855, Georg Thieme Verlag Stuttgart (1981) Summary Only.

Kreider, J.W., et al., "Concordance of Condylomata Acuminata Responses to Treatment with Intralesional MPI 5003 and Papiloma Responses in the Shope Rabbit Papilloma Model System," *Skin Pharmacol. 5*:201–202, Karger AG, Basel (1992).

Ksander, G.A., et al., "The effect of platelet releasate on wound healing in animal models," *J. Am. Acad. Dermatol. 22*:781–791, Amedo Group (1990).

Larson, M.J., et al., "Efficacy of a Fibrin Hemostatic Bandage in Controlling Hemorrhage From Experimental Arterial Injuries," *Arch. Surg. 130*:420–422, American Medical Association (1995).

Lasa, C., et al., "Osterregeneration Using a Fibrin Sealant Delivery Vehicle for Demineralized Bone Matrix," *J. Cell. Biochem. Suppl. 17E*:162 Abstract No. RZ 217 (Mar. 29–Apr. 4, 1993).

Lasa, C.I., et al., "Effect of Fibrin Glue and Opsite on Open Wounds in DB/DB Mice," *J. Surg. Res. 54*:202–206, Academic Press, Inc. (1993).

Lerner, R., and Binur N.S., "Current Research Review. Current Status of Surgical Adhesives," *J. Surg. Res. 48*:165–181, Academic Press, Inc. (1990).

Lindner, V., et al., "Basic Fibroblast Growth Factor Stimulates Endothelial Regrowth and Proliferation in Denuded Arteries," *J. Clin. Invest. 85*:2004–2008, The American Society for Clinical Investigation, Inc. (1990).

Lobb, R.R., "Clinical applications of heparin–binding growth factors," *Eur. J. Clin. Invest. 18*:321–336, Blackwell Science Ltd. (1988).

Lucht, U., et al., "Fibrin sealant in bone transplantation," *Acta. Orthop. Scand. 57*:19–24, Scandinavian University Press (1986).

Luyten, F.P., et al., "Purification and Partial Amino Acid Sequence of Osteogenin, a Protein Initiating Bone Differentiation," *J. Biol. Chem. 264*:13377–13380, American Society of Biochemistry and Molecular Biology Inc. (1989).

Lynch, S.E., et al., "Growth Factors in Wound Healing," *J. Clin. Invest. 84*:640–646, The American Society for Clinical Investigation, Inc. (1989).

MacPhee, M., et al., "Fibrin Sealant Based Bandages and Foam: Hemostatic Devices for Treatment of Combat Casualties on the Battlefield," Presented at the Advanced Technology Applications to Combat Casualty Care (ATACCC) conference (May 17–18, 1995).

MacPhee, M., "Field–Ready Fibrin Sealant Based Hemostatic Devices," presented at the 29th Penner Blood Conference (May 1995).

MacPhee, M., et al., "Fibrin Sealant Based Hemostatic Devices for Treatment of Trauma in the Field," presented at the FDA–Army Conference on Fibrin Sealant (Dec. 1994).

Mark, D.E., et al., "Repair of Calvarial Nonunions by Osteogenin, a Bone–Inductive Protein," *Plast. Reconstr. Surg. 86*:623–630, Lippincott Williams & Wilkins (1990).

Massagué, J., "The TFG–β Family of Growth and Differentiation Factors," *Cell 49*:437–438, Cell Press(1987).

Matras, H., "Fibrin Seal: The State of the Art," *J. Oral. Maxillofac. Surg. 43*:605–611, W.B. Saunders Co. (1985).

McEvitt, W.G., "Experiences with Fibrin Fixation Methods of Skin Grafting. A Clinical Evaluation," *J. Mich. State Med. Assoc. 44*:1347–1351, Michigan State Medical Society (1945).

McGee, G.S., et al., "Recombinant Basic Fibroblast Growth Factor Accelerates Wound Healing," *J. Surg. Res. 45*:145–153, Academic Press, Inc. (1988).

Michael, P., and Abbot, W., "The Use of Human Fibrinogen in Reconstructive Surgery," *J.A.M.A. 123*:279, The American Medical Association (1943).

Miller, B.H., et al., "Basal cell carcinoma histologically resolved after treatment with intralesional 5–Fluorouracil Therapeutic Implant," *Proc. of the Amer. Assoc. for Cancer Res. 32*:420 Abstract No. 2496, The American Association for Cancer Research (1991).

Montesano, R., et al., "Basic fibroblast growth factor induces angiogenesis in vitro," *Proc. Natl. Acad. Sci. USA 83*:7297–7301, The National Academy of Science (1986).

Moore, T.D., and Sweetser, Jr., T.H., "Coagulum Pelviolithotomy; an Improved Technique," *J. Urol. 67*:579–584, The Williams & Wilkins Company (1952).

Moore, W.S., et al., "Development of an Infection–Resistant Vascular Prosthesis," *Arch. Surg. 116*:1403–1407, American Medical Association (1981).

Morrison, P.R., and Singer, M., "Chemical, Clinical, and Immunological Studies on the Products of Human Plasma Fractionation. XVII. A Note on the Absorption Rates of Fibrin Films in Tissue," *J. Clin. Invest. 23*:573–575, The American Society for Clinical Investigation (1944).

Mustoe, T.A., et al., "Accelerated Healing of Incisional Wounds in Rats Induced by Transforming Growth Factor–β," *Science 237*:1333–1336, American Association for the Advancement of Science (1987).

Nowotny, R., et al., "Mechanical Properties of Fibrinogen–Adhesive Material," *Biomaterials 3*:677–682, John Wiley & Sons Ltd. (1982).

Orenberg, E.K., et al., "The effect of intralesional 5–Fluorouracil Therapeutic Implant (MPI 5003) for treatment of basal cell carcinoma," *J. Am. Acad. Dermatol. 27*:723–728, American Academy of Dermatology (1992).

Petrelli, N.J., et al., "The Application of Tissue Adhesives in Small Bowel Anastomoses," *J. Surg. Oncol. 19*:59–61, Alan R. Liss, Inc. (1982).

Pierce, G.F., et al., "In Vivo Incisional Wound Healing Augmented by Platelet–Derived Growth Factor and Recombinant ti c–sis Gene Homodimeric Proteins," *J. Exp. Med. 167*:974–987, The Rockefeller University Press (1988).

Pop, M., et al., "Experimental covering of the dental pulp in the dog with biological substances," *Chemical Abstracts 72*:209 Abstract No. 119944n, The American Chemical Society (1970).

Presta, M., et al., "Basic fibroblast growth factor requires a long–lasting activation of protein kinase C to induce cell proliferation in transformed fetal bovine aortic endothelial cells," *Cell Regul. 2*:719–726, The American Society for Cell Biology (1991).

Puumala, M., et al., "Intraventricular infusion of HBGF–2 promotes cerebral angiogenesis in Wistar Rat," *Brain Res. 534*:283–286, Elsevier Science Publishers B.V. (1990).

Radomski, J.S., et al., "Initial Adherence of Human Capillary Endothelial Cells to Dacron," *J. Surgical Res. 42*:133–140, Academic Press, Inc. (1987).

Ramalanjaona, G., et al., "The effect of fibronectin coating on endothelial cell kinetics in polytetrafluoroethylene grafts," *J. Vasc. Surg. 3*:264–272, Mosby–Year Book Inc. (1986).

Redl, H., et al., "In vitro properties of mixtures of fibrin seal and antibiotics," *Biomaterials 4*:29–32, Butterworth & Co. (1983).

Roberts, A.B., and Sporn, M.B., "Transforming Growth Factor β," *Adv. Cancer Res. 51*:107–145, Academic Press Inc. (1988).

Rothe, M., and Falanga, V., "Growth Factors. Their Biology and Promise in Dermatologic Diseases and Tissue Repair," *Arch. Dermatol. 125*:1390–1398, American Medical Association (1989).

Rovee, D.T., "Evolution of Wound Dressings and their Effects on the Healing Process," *Clin. Mater. 8*:183–188, Elsevier Science Publishers Ltd. (1991).

Sakurai, T., et al., "Controlled release of sisomicin from fibrin glue," *J. Control. Release 18*:39–44, Elsevier Science Publishers B.V. (1992).

Sauvage, L.R., et al., "Interspecies Healing of Porous Arterial Prostheses. Observations, 1960 to 1974," *Arch. Surg.* 109:698–705, American Medical Association (1974).

Schlag, G., and Redl, H.G., "Fibrin Sealant in Orthopedic Surgery," *Clin. Orthop.* 227:269–285, Lippincott Williams & Wilkins (1988).

Schrenk, P., et al., "Fibrin Glue Coating of e-PTFE Prosthesis Enhances Seeding of Human Endothelial Cells," *Thorac. cardiovasc. Surgeon* 35:6–10, Georg Thieme Verlag Stuttgart (1987).

Schultz, G.S., et al., "Epithelial Wound Healing Enhanced by Transforming Growth Factor–α and Vaccinia Growth Factor," *Science* 235:350–352, American Association for the Advancement of Science (1987).

Schwarz, N., et al., "The Influence of Fibrin Sealant on Demineralized Bone Matrix–Dependent Osteoinduction," *Clin. Orthop.* 238:282–287, Lippincott Williams & Wilkins (1989).

Senderhoff, R.L., et al., "Fibrin Based Drug Delivery Systems," *J. Parental Sci. Tech.* 45:2–6, Parenteral Drug Association (1991).

Sheehan, J.E., "Plasma Fixation of Skin Grafts," *Am. J. Surg.* 65:74–78, The American Journal of Surgery, Inc. (1944).

Shindo, S., et al., "Improved patency of collagen–impregnated grafts after in vitro autogenous endothelial cell seeding," *J. Vasc. Surg.* 6:325–332, Mosby–Year Book, Inc. (1987).

Shoemaker, S.C., et al., "Effects of fibrin sealant on incorporation of autograft and xenograft tendons within bone tunnels," *Am. J. Sports Med.* 17:318–324, American Orthopaedic Society for Sports Medicine (1989).

Silbermann, M., "In vitro systems for inducers of cartilage and bone development," *Biomaterials* 11:47–49, Butterworth–Heinemann Ltd. (1990).

Silberstein, L.E., et al., "An autologous fibrinogen–based adhesive for use in otologic surgery," *Transfusion* 28:319–321, American Association of Blood Banks (1988).

Spotnitz, W.D., et al., "Fibrin Glue from Stored Human Plasma. An Inexpensive and Efficient Method for Local Blood Bank Preparation," *Am. Surg.* 53:460–462, Southeastern Surgical Congress (1987).

Sprugel, K.H., et al., "The Effects of Different Growth Factors in Subcutaneous Wound Chambers," in *Growth Factors and Other Aspects of Wound Healing: Biological and Clinical Implications*, Barbul, A., et al., eds., Alan R.Liss, Inc., New York, NY, pp. 77–91 (1988).

Stark, J., and de Leval, M., "Experience with Fibrin Seal (Tisseel) in Operations for Congenital Heart Defects," *Ann. Thorac. Surg.* 38:411–413, Elsevier Science Inc. (1984).

Stemberger, A., and Blumel, G., "Fibrinogen–Fibrin Conversion and Inhibition of Fibrinolysis," *Thorac. cardiovasc. Surgeon* 30:209–214, Georg Thieme Verlag Stuttgart (1982).

Sugie, I., et al., "The chemical modification of fibrin film as artificial skin," *Chemical Abstracts* 85:318, Abstract No.182381k, The American Chemical Society (1976).

Sugitachi, A., et al., "A Newly Designed Anticancer Tumor Immunity Drug Delivery System," *Trans. Am. Soc. Artif. Intern. Organs* 37:M177–M178, American Society For Artificial Internal Organs (1991).

Thompson, D.F., et al., "Fibrin Glue: A Review of Its Preparation, Efficacy, and Adverse Effects as a Topical Hemostat," *Drug Intell. Clin. Pharm.* 22:946–952, Cincinnati OH Drug Intelligence (1988).

Thompson, J.A., et al., "Site–Directed Neovessel Formation in Vivo," *Science* 241:1349–1352, American Associated for the Advancement of Science (1988).

Thompson, J.A., et al., "Heparin–binding growth factor 1 induces the formation of organoid neovascular structures in vivo," *Proc. Natl. Acad. Sci. USA* 86:7928–7932, The National Academy of Sciences (1989).

Thorson, G.K., et al., "The Role of the Tissue Adhesive Fibrin Seal (FS) in Esophageal Anastomoses," *J. Surg. Oncol.* 24:221–223, Alan R. Liss, Inc. (1983).

Tidrick, R.T., and Warner, E.D., "Fibrin Fixation of Skin Transplants," *Surgery* 15:90–95, The C.V. Mosby Company (1944).

Tsuboi, R., and Rifkin, D.B., "Recombinant Basic Fibroblast Growth Factor Stimulates Wound Healing in Healing–impaired db/db Mice," *J. Exp. Med.* 172:245–251, The Rockefeller University Press (1990).

Ulatowski, L., et al., "Neue Aspekte der Anwendung eines erweiterten Fibrinklebesystems (FKS)," *Orthop. Praxis* 15:795–799, Kluwer Academic (1979).

Urist, M.R., and Strates, B.S., "Bone Formation in Implants of Partially and Wholly Demineralized Bone Matrix," *Clin. Orthop.* 71:271–278, Lippincott Williams & Wilkins (1970).

Urist, M.R., et al., "Bone Morphogenesis in Implants of Insoluble Bone Gelatin," *Proc. Natl. Acad. Sci. USA* 70:3511–3515, The National Academy of Sciences (1973).

Walterbusch, G., et al., "Clinical Experience with Fibrin Glue for Local Bleeding Control and Sealing of Vascular Prostheses," *Thorac. cardiovasc. Surgeon* 30:234–235, Georg Thieme Verlag Stuttgart (1982).

Wang, E.A., et al., "Bone Morphogenetic Proteins and Bone Repair," *J. Cell Biochem. Suppl.* 0(15 Part F):161, Kluwer Academic (1991).

Watkins, M.T., et al., "Adult Human Saphenous Vein Endothelial Cells: Assessment of Their Reproductive Capacity for Use in Endothelial Seeding of Vascular Prostheses," *J. Surg. Res.* 36:588–596, Academic Press, Inc. (1984).

Weiner, L., and Wald, A.H., "Fibrin Foam and Thrombin as Used in the Surgical Removal of a Large Fibromyxoma of the Mandible," *J. Am. Dent. Assoc.* 33:731–735, American Dental Association (1946).

Weisman, R.A., et al., "Biochemical Characterization of Autologous Fibrinogen Adhesive," *Laryngoscope* 97:1186–1190, Lippincott Williams & Wilkins (1987).

Williams, S.K., et al., "Adult Human Endothelial Cell Compatibility with Prosthetic Graft Material," *J. Surgical Res.* 38:618–629, Academic Press, Inc. (1985).

Woodhall, B., "Fibrin Foam as a Hemostatic Agent in Rehabilitation Neurosurgery," *J.A.M.A.* 126:469–471, The American Medical Association (1944).

Yu, N., et al., "Comparison of Antitumor Effects of Treatment Sequence of Fluorouracil (FU) and Cisplatin (Pt) Therapeutic Implants in a Mouse Tumor Model," *Proc. Annu. Meet. Am. Soc. Clin. Oncol.* 11:100 Abstract No. 223, American Society of Clinical Oncology (Mar. 1992).

Yu, N., et al., "Pharmacokinetics and Clinical Application of the Intralesional Methotrexate Therapeutic Implant," *Proc. Annu. Meet. Am. Soc. Clin. Oncol.* 11:100 Abstract No. 222, American Society of Clinical Oncology (Mar. 1992).

Zilla, P., et al., "Use of fibrin glue as a substrate for in vitro endothelialization of PTFE vascular grafts," *Surgery* 105:515–522, Mosby–year Book Inc. (1989).

Zilch, H., and Lambris, E., "The Sustained Release of Cefotaxim from a Fibrin–Cefotaxim Compound in Treatment of Osteitis," *Arch. Orthop. Trauma Surg. 106*:36–41, Springer–Verlag (1986).

World Patents Index English translation of title and abstract of Japanese patent application JP 54–104687 (AN1).

World Patents Index English translation of title and abstract of German patent application DE 3,037,270 (A02).

World Patents Index English translation of title and abstract of Japanese patent application JP 60–204725 (AP3).

English Translation of JP 62–246370, translated by Translation Services PTY Ltd, translation dated Mar. 6, 2001 (AL5).

English Translation of JP 63–115564, translated by Translation Services PTY Ltd, translation dated Mar. 13, 2001 (AO5).

English Translation of the first full paragraph at p. 28 of Afra, D. et al., "Experimentelle Untersuchung der Resorption von Fibrinfilmen und ihre Anwendung in der neurochirurgischen Praxis", *Acta Med. Acad. Sci. Hung. 11*:1–29, Hungarian Academy of Science (1958), translated by McElroy Translation Company (dated Aug. 24, 2001).

English Translation of the second–fifth paragraphs at p. 852 of Bagdy, D. et al., "Experimentelle und klinische Anwendung der aus Rinderplasma hergesteliten Fibrinprodukte," *Zentralblatt für Chirurgie 77*:848–852, Vereinigung Mittelrheinischer Chirurgen (1952), translated by McElroy Translation Company (dated Aug. 24, 2001).

English Translation of the fourth–sixth paragraphs at p. 152 and the sixth paragraph at p. 184 of Bagdy D. et al., in *Thrombin–Fibrinprodukte und Ihre Therapeutische Anwendung*, pp. 152–159, 184–187, Veb Gustav Fischer Verlag Jena (1963), translated by McElroy Translation Company (dated Aug. 24, 2001).

English Translation of the first full column at p. 219 of István, L. et al., "Gastrointestinalis vérzések csillapítása thrombin–fibrin készítménnyel," *Orv. Hetil. 105*:219–223, Markusovszky Lajos Foundation (1964), translated by McElroy Translation Company (dated Aug. 24, 2001).

English Translation of the third–fourth paragraphs at p. 615 of Stoll, H.G., "Koagulum–Pyelolithotomie," *Zeitschrift fër Urologie 52*:610–615, Veb Georg Thieme Leipzig (1959), translated by McElroy Translation Company (Aug. 24, 2001).

English Translation of the fourth–eighth paragraphs at p. 479 of Winter, L. et al., "Experimentelle und klinische Anwendung der aus Rinderplasma hergestellten Fibrinprodukte. III. Klinische Verwendung von hämostatischen Fibrinprodukten," *Zentralblatt für Chirurgie 78*:469–479, Vereinigung Mittelrheinischer Chirurgen (1953), translated by McElroy Translation Company (dated Aug. 24, 2001).

Co–pending U.S. application No. 08/474,078, MacPhee et al., filed Jun. 7, 1995.

* cited by examiner

HEMOSTATIC SANDWICH BANDAGE

This application is a 371 of PCT/US99/10952, May 19, 1999, which claims benefit of 60/085,931, may 19, 1998.

I. FIELD OF THE INVENTION

The present invention relates to a hemostatic sandwich bandage which comprises a plurality of layers that contain resorbable materials and/or coagulation proteins. The inventive hemostatic sandwich bandage is useful for the treatment of wounded tissue.

II. BACKGROUND OF THE INVENTION

The control of hemorrhage (bleeding) is a critical step in first aid and field trauma care. Unfortunately, the materials and methods available to stop bleeding in prehospital care (gauze dressings, direct pressure, and tourniquets) have not changed greatly in the past 2000 years. L. Zimmerman et al., *Great Ideas in the History of Surgery* (San Francisco, Calif.: Norman Publishing; 1993), 31. Even in good hands they are not uniformly effective, and the occurrence of excessive bleeding or fatal hemorrhage from an accessible site is not uncommon. J. M. Rocko et al., *J. Trauma* 22:635 (1982).

Mortality data from Vietnam indicates that 10% of combat deaths were due to uncontrolled extremity hemorrhage. *SAS/STAT Users Guide*, 4th ed. (Cary, N.C.: SAS Institute Inc; 1990). Up to one third of the deaths from exsanguination during the Vietnam War could have been prevented by the use of effective field hemorrhage control methods. *SAS/STAT Users Guide*, 4th ed. (Cary, N.C.: SAS Institute Inc; 1990).

Although civilian trauma mortality statistics do not provide exact numbers for prehospital deaths from extremity hemorrhage, case and anecdotal reports indicate similar occurrences. J. M. Rocko et al., *J. Trauma* 22:635 (1982). These data suggest that a substantial increase in survival can be effected by the prehospital use of a simple and effective method of hemorrhage control.

Liquid fibrin sealants have been used for years as an operating room adjunct for hemorrhage control. J. L. Garza et al., *J. Trauma* 30:512–513 (1990); H. B. Kram et al., *J. Trauma* 30:97–101(1990); M. G. Ochsner et al., *J. Trauma* 30:884–887 (1990); T. L. Matthew et al., *Ann. Thorac. Surg.* 50:40–44 (1990); H. Jakob et al., *J. Vasc. Surg.*, 1:171–180 (1984). The first mention of tissue glue used for hemostasis dates back to 1909. *Current Trends in Surgical Tissue Adhesives: Proceedings of the First International Symposium on Surgical Adhesives*, M. J. MacPhee et al., eds. (Lancaster, Pa.: Technomic Publishing Co; 1995). The widespread use of fibrinogen and thrombin was common in the last year of World War II, but was abandoned because of the transmission of hepatitis. D. B. Kendrick, *Blood Program in WW II* (Washington. D.C.: Office of the Surgeon General, Department of Army; 1989). 363–368.

Currently, single donor fibrin sealants are widely used clinically, not only for hemorrhage control but in various surgical situations. W. D. Spotnitz, *Thromb. Haemost.* 74:482–485 (1995); R. Lerner et al., *J. Surg. Res.* 48:165–181 (1990). Even more extensive use is limited by the strict requirements for temperature control, availability of thawed blood components, and the need for mixing of components. Additional problems with the standard fibrin sealants stem from the transfusion risk of human cryoprecipitate (E. M. Soland et al., *JAMA* 274:1368–1373 (1995)), the low and variable amounts of fibrinogen in the cryoprecipitate (10–30 mg) (P. M. Ness et al., *JAMA* 241:1690–1691 (1979)), hypotensive responses to bovine thrombin (R. Berguer et al., *J. Trauma* 31:408–411 (1991)) and antibody responses to bovine thrombin (S. J. Rapaport et al., *Am. J. Clin. Pathol.* 97:84–91 (1992)).

The American Red Cross and others have developed plasma protein purification methods that seem to eliminate the hepatitis risk. R. F. Reiss et al., *Trans. Med. Rev.* 10:85–92 (1996). These products are presently being considered for approval by the Food and Drug Administration.

A dry fibrinogen-thrombin dressing (TACHOCOMB™, Hafslund Nycomed Pharma, Linz, Austria) is also available for operating room use in many European countries. U. Schiele et al., *Clin. Materials* 9:169–177 (1992). Present formulations of this dressing use bovine thrombin. While this fibrinogen-thrombin dressing requires no premixing and is easy to use, its utility for field applications is limited by a requirement for storage at 4° C. and the necessity for prewetting with saline solution prior to application to the wound.

III. SUMMARY OF THE INVENTION

It is therefore an object of the present invention to provide a hemostatic sandwich bandage that can be used for wound healing. Other objects, features and advantages of the present invention will be set forth in the detailed description of preferred embodiments that follows, and in part will be apparent from the description or may be learned by practice of the invention. These objects and advantages of the invention will be realized and attained by the compositions and methods particularly pointed out in the written description and claims hereof.

In accordance with these and other objects, a first embodiment of the present invention is directed to a hemostatic sandwich bandage for treating wounded tissue in a patient which comprises: (i) a first fibrinogen layer; (ii) a thrombin layer adjacent to the first fibrinogen layer; and (iii) a second fibrinogen layer adjacent to the thrombin layer.

A second embodiment of the present invention is directed to a hemostatic sandwich bandage for treating wounded tissue in a patient which comprises: (i) a resorbable material layer; (ii) a first fibrinogen layer adjacent to the resorbable material layer; (iii) a thrombin layer adjacent to the first fibrinogen layer; and (iv) a second fibrinogen layer adjacent to the thrombin layer.

A third embodiment of the present invention is directed to a hemostatic sandwich bandage or treating wounded tissue in a patient which comprises: (i) a first fibrinogen layer; (ii) a resorbable material layer adjacent to the first fibrinogen layer; (iii) a thrombin layer adjacent to the resorbable material layer; and (iv) a second fibrinogen layer adjacent to the thrombin layer.

A fourth embodiment of the present invention is directed to a hemostatic sandwich bandage for treating wounded in a patient which comprises: (i) a resorbable material layer; and (ii) a thrombin layer adjacent to the resorbable material layer. The resorbable material layer may also optionally contain fibrinogen.

A fifth embodiment of the present invention is directed to a hemostatic sandwich bandage for treating wounded in a patient which comprises: (i) a first resorbable material layer; (ii) a second resorbable material layer adjacent to the first resorbable material layer; and (iii) a thrombin layer adjacent to the second resorbable material layer. The resorbable material layers may also optionally contain fibrinogen.

Each layer of the inventive hemostatic bandages may also optionally contain one or more suitable fillers, binding agents and/or solubilizing agents. In addition, each of the inventive hemostatic bandages may also optionally further comprise a release layer which contains a release agent and/or a backing material.

A sixth embodiment of the present invention is directed to methods for treating wounded tissue in a patient, which comprises applying any of the inventive hemostatic sandwich bandages to the wounded tissue.

It is to be understood that both the foregoing general description and the following detailed description are exemplary and explanatory only and are intended to provide further explanation of the invention as claimed.

IV. DETAILED DESCRIPTION OF THE PREFERRED EMBODIMENTS

A. Definitions

Unless defined otherwise, all technical and scientific terms used herein have the same meaning as is commonly understood by one of skill in the art to which this invention belongs. All patents and publications mentioned herein are incorporated by reference.

"Patient" as used herein refers to human or animal individuals in need of medical care and/or treatment.

"Wound" as used herein refers to any damage to any tissue of a patient that results in the loss of brood from the circulatory system. The tissue may be an internal tissue, such as an organ or blood vessel, or an external tissue, such as the skin. The loss of blood may be internal, such as from a ruptured organ, or external, such as from a laceration. A wound may be in a soft tissue, such as an organ, or in hard tissue, such as bone. The damage may have been caused by any agent or source, including traumatic injury, infection or surgical intervention.

"Resorbable material" as used herein refers to a material that is broken down spontaneously and/or by the mammalian body into components which are consumed or eliminated in such a manner as not to interfere significantly with wound healing and/or tissue regeneration, and without causing any significant metabolic disturbance.

"Stability" as used herein refers to the retention of those characteristics of a material that determine activity and/or function.

"Binding agent" as used herein refers to a compound or mixture of compounds that improves the adherence of one layer of the inventive hemostatic sandwich bandage to one or more different layers and/or the adherence of the components of a given layer to other components of that layer.

"Solubilizing agent" as used herein refers to a compound or mixture of compounds that improves the dissolution of a protein or proteins in aqueous solvent.

"Filler" as used herein refers to a compound or mixture of compounds that provide bulk and/or porosity to one or more layers of the inventive hemostatic sandwich bandages.

"Release agent" as used herein refers to a compound or mixture of compounds that facilitates removal of an inventive hemostatic sandwich bandage from a manufacturing mold.

"Foaming agent" as used herein refers to a compound or mixture of compounds that produces gas when hydrated under suitable conditions.

B. Preferred Embodiments

A first preferred embodiment of the present invention is directed to a hemostatic sandwich bandage for treating wounded tissue in a patient which comprises:(i) a first fibrinogen layer; (ii) a thrombin layer adjacent to the first fibrinogen layer; and (iii) a second fibrinogen layer adjacent to the thrombin layer.

A second embodiment of the present invention is directed to a hemostatic sandwich bandage for treating wounded tissue in a patient which comprises: (i) a resorbable material layer; (ii) a first fibrinogen layer adjacent to the resorbable material layer; (iii) a thrombin layer adjacent to the first fibrinogen layer; and (iv) a second fibrinogen layer adjacent to the thrombin layer.

A third embodiment of the present invention is directed to a hemostatic sandwich bandage for treating wounded tissue in a patient which comprises: (i) a first fibrinogen layer; (ii) a resorbable material layer adjacent to the first fibrinogen layer; (iii) a thrombin layer adjacent to the resorbable material layer; and (iv) a second fibrinogen layer adjacent to the thrombin layer.

A fourth embodiment of the present invention is directed to a hemostatic sandwich bandage for treating wounded in a patient which comprises: (i) a resorbable material layer; and (ii) a thrombin layer adjacent to the resorbable material layer. The resorbable material layer may also optionally contain fibrinogen.

A fifth embodiment of the present invention is directed to a hemostatic sandwich bandage for treating wounded in a patient which comprises: (i) a first resorbable material layer; (ii) a second resorbable material layer adjacent to the first resorbable material layer; and (iii) a thrombin layer adjacent to the second resorbable material layer. The resorbable material layers may also optionally contain fibrinogen.

Each layer of the inventive hemostatic sandwich bandages may also optionally contain one or more suitable fillers, such as sucrose.

Each layer of the inventive hemostatic sandwich bandages may also optionally contain one or more suitable binding agents, such as sucrose.

Each layer of the inventive hemostatic sandwich bandages may also optionally contain one or more suitable solubilizing agents, such as sucrose.

Each layer of the inventive hemostatic sandwich bandages may also optionally contain one or more suitable foaming agents, such as a mixture of citric acid and sodium bicarbonate.

Each of the inventive hemostatic sandwich bandages may also optionally further comprise a release layer which contains a release agent. A preferred release agent is sucrose.

Each of the inventive hemostatic sandwich bandages may also further comprise a backing material on the side of the bandage opposite the wound-facing side. The backing material may be affixed with a physiologically-acceptable adhesive or may be self-adhering (e.g by having a sufficient surface static charge). The backing material may be a resorbable material or a non-resorbable material, such as a silicone patch or plastic. Preferably, the backing material is a resorbable material.

The fibrinogen employed in the inventive hemostatic sandwich bandage is preferably Topical Fibrinogen Complex (TFC), but any suitable fibrinogen, or derivative or metabolite thereof (such as fibrinopeptide A and fibrinopeptide B), may be employed as desired. A specific fibrinogen (or fibrinogen-containing composition) for a particular application may be selected empirically by one skilled in the art. The fibrinogen may also contain Factor XIII.

TFC is a mixture of human plasma proteins which have been purified to an appropriate level and virally inactivated. A preferred aqueous solution of TFC contains 100–130 mg/mL total protein, of which at least 80% is fibrinogen. Other constituents of TFC include albumin (generally about 5–25 mg/mL), plasminogen (generally about 5 mg/mL); Factor XIII (generally about 10–40 Units/mL); and polysorbate 80 (no more than 3%). The pH of TFC is generally in the range of 7.1–7.5. Suitable TFC may also contain fibronectin.

The thrombin employed in the inventive hemostatic bandage is preferably a lyophilized mixture of human plasma proteins which have been purified to an appropriate level and virally inactivated. A preferred aqueous solution of thrombin contains thrombin at a potency of about 300±50 International Units/mL. Other constituents include albumin (generally about 5 mg/mL) and glycine (generally about 0.3 M±0.05M). The pH of the preferred thrombin is generally in the range of 6.5–7.1.

Additionally, in each of the embodiments of the present invention, thrombin may be replaced by any of the agents known by those skilled in the art to be activators of fibrin formation. Illustrative examples of such agents are snake venoms. A specific activator of fibrin formation for a particular application may be selected empirically by one skilled in the art.

Any suitable resorbable material known to those skilled in the art may be employed in the present invention. For example, the resorbable material may be a proteinaceous substance, such as silk, fibrin, keratin, collagen and/or gelatin, or a carbohydrate substances, such as alginates, chitin, cellulose, proteoglycans (e.g. poly-N-acetyl glucosamine), glycolic acid polymers, lactic acid polymers, or glycolic acid/lactic acid co-polymers. Specific resorbable material(s) for a particular application may be selected empirically by those skilled in the art.

Preferably, the resorbable material is a carbohydrate substance. Illustrative examples of particularly preferred resorbable materials are sold under the tradenames VICRYL™ (Poly(Lactide-Co-Glycoside), a glycolic acid/lactic acid copolymer) and DEXON™ (glycolic acid polymer).

The various layers of the inventive hemostatic sandwich bandage may be affixed to one another by any suitable means known and available to those skilled in the art. Preferably, the fibrinogen layer(s) and/or the thrombin layer (s) is (are) applied as a series of quick-frozen aqueous solution layers and subsequently lyophilized or freeze-dried.

In a particularly preferred embodiment of the present invention, when the inventive bandages are prepared using a mold, a release agent, such as sucrose, is applied to the mold before the first layer of the bandage being prepared. In such embodiments, the inventive hemostatic sandwich bandage further comprises a release layer, which contains said release agent, adjacent to the (i) layer and on the opposite side from the (ii) layer.

Alternatively, a physiologically-acceptable adhesive may applied to the resorbable material and/or the backing material (when present) and the fibrinogen layer(s) and/or the thrombin layer(s) subsequently affixed thereto.

In one embodiment of the inventive sandwich bandage, the physiologically-acceptable adhesive has a shear strength and/or structure such that the resorbable material and/or backing material can be separated from the fibrinogen layer and/or the thrombin layer after application of the bandage to wounded tissue. In another embodiment, the physiologically-acceptable adhesive has a shear strength such that the resorbable material and/or backing material cannot be separated from the fibrinogen layer and/or the thrombin layer after application of the bandage to wounded tissue.

Suitable fibrinogen and thrombin may be obtained from human or mammalian plasma by any of the purification methods known and available to those skilled in the art; from supernatants or pastes of recombinant tissue culture, viruses, yeast, bacteria, or the like that contain a gene that expresses a human or mammalian plasma protein which has been introduced according to standard recombinant DNA techniques; or from the fluids (e.g. blood, milk, lymph, urine or the like) of transgenic animals that contain a gene that expresses human fibrinogen and/or human thrombin which has been introduced according to standard transgenic techniques.

As a general proposition, the purity of the fibrinogen and/or the thrombin for use in the inventive hemostatic sandwich bandage will preferably be an appropriate purity known to one of ordinary skill in the relevant art to lead to the optimal efficacy and stability of the protein. Preferably, the fibrinogen and/or the thrombin has been subjected to multiple chromatographic purfication steps, such as affinity chromatography and preferably immunoaffinity chromatography, to remove substances which cause fragmentation, activation and/or degradation of the fibrinogen and/or the thrombin during manufacture, storage and/or use. Illustrative examples of such substances that are preferably removed by purification include protein contaminants, such as inter-alpha trypsin inhibitor and pre-alpha trypsin inhibitor; non-protein contaminants, such as lipids; and mixtures of protein and non-protein contaminants, such as lipoproteins.

The concentration of the fibrinogen and/or the thrombin employed in the inventive hemostatic sandwich bandage is also preferably selected to optimize both the efficacy and stability thereof, as may be determined empirically by one skilled in the relevant art. During use of the inventive hemostatic sandwich bandage, the fibrinogen and the thrombin are preferably activated at the time the bandage is applied to the wounded tissue by the endogenous fluids of the patient escaping from the hemorrhaging wound. Alternatively, in situations where fluid loss from the wounded tissue is insufficient to provide adequate hydration of the protein layers, the fibrinogen and or the thrombin may be activated by a suitable, physiologically-acceptable liquid, optionally containing any necessary co-factors and/or enzymes, prior to or during application of the hemostatic sandwich bandage to the wounded tissue.

In addition, one or more supplements may also be contained in one or more layers of the inventive hemostatic sandwich bandage, such as growth factors, drugs, polyclonal and monoclonal antibodies and other compounds. Illustrative examples of such drugs include, but are not limited to: antibiotics, such as tetracycline and ciprofloxacin, amoxicillin, and metronidazole; anticoagulants, such as activated protein C, heparin, prostacyclin ($PGI_2$), prostaglandins, leukotrienes, antithrombin III, ADPase, and plasminogen activator; steroids, such as dexamethasone, inhibitors of prostacyclin, prostaglandins, leukotrienes and/or kinins to inhibit inflammation; cardiovascular drugs, such as calcium channel blockers, vasodilators and vasoconstrictors; chemoattractants; local anesthetics such as bupivacaine; and antiproliferative/antitumor drugs such as 5-fluorouracil (5-FU), taxol and/or taxotere; antivirals, such as gangcyclovir, zidovudine, amantidine, vidarabine, ribaravin, trifluridine, acyclovir, dideoxyuridine and antibodies to viral components or gene products; cytokines, such as $\alpha$- or $\beta$- or $\gamma$-Interferon, $\alpha$- or $\beta$-tumor necrosis factor, and interleukins; colony stimulating factors; erythropoietin; antifungals, such as diflucan, ketaconizole and nystatin; antiparasitic gents, such as pentamidine; anti-inflammatory agents, such as $\alpha$-1-anti-trypsin and $\alpha$-1-antichymotrypsin; anesthetics, such as bupivacaine; analgesics; antiseptics; and hormones. Other illustrative supplements include, but are not limited to: vitamins and other nutritional supplements; glycoproteins; fibronectin; peptides and proteins; carbohydrates (both simple and/or complex); proteoglycans; antiangiogenins; antigens; lipids or liposomes; oligonucleotides (sense and/or antisense DNA and/or RNA); and gene therapy reagents.

The following examples are illustrative only and are not intended to limit the scope of the invention as defined by the appended claims. It will be apparent to those skilled in the art that various modifications and variations can be made in the methods of the present invention without departing from the spirit and scope of the invention. Thus, it is intended that the present invention cover the modifications and variations of this invention provided they come within the scope of the appended claims and their equivalents.

All patents and publications referred to herein are expressly incorporated by reference.

V. EXAMPLES

A. Example I

Fibrinogen and thrombin vials were removed from a refrigerator and allowed to warm to room temperature for 2 hours. To each vial of thrombin 2 mL of 40 mM $CaCl_2$ was added; this yielded a final concentration of 505 U/mL of thrombin. DISPO™ molds (Baxter) size 3.0×2.4 cm were placed on a freezing tray on top of dry ice.

To each of 12 molds, 1.75 mL of $H_2O$ was added and allowed to freeze for 1 hour at −80° C. Once frozen 140 μL of thrombin (70 units) was pipetted on top of the $H_2O$ and allowed to freeze for an additional 1 hour at −80° C. Fibrinogen was solubilized with water (8 mL) to a concentration of 50 mg/mL. To the molds 1.1 mL of fibrinogen was added (55 mg) and allowed to freeze for an additional 1 hour at −80° C., followed by the addition of 1 mL of $H_2O$. The bandages were allowed to freeze for 1 hour at −80° C. Then 0.25 ml of thrombin (125 units) was added and allowed to freeze for one hour. An additional 1.1 mL of fibrinogen (55 mg) was pipetted on top and allowed to freeze for 1 hour.

Once all materials were added and frozen, VICRYL™ was placed on top and pressed into place by gentle finger pressure. To cover the VICRYL™, 500 μL of 30% sucrose was added and allowed to freeze. The bandages were placed at −80° C. for 2 hours, then placed into the freeze dryer. Upon completion, the vacuum was released and the bandages were removed and examined.

RESULTS: The bandages when removed from the freeze dryer were uniform and consistent; the VICRYL™ was attached and all layers were intact.

B. Example II

The fibrinogen and thrombin vials were removed from the refrigerator and allowed to warm to room temperature for 2 hours. VICRYL™ was applied and pressed into DISPO™ plastic molds (2.4 cm×2.4 cm). The molds were incubated at −80° C. for 1 hour.

Thrombin was solubilized with 0.5 mL of 40 mM $CaCl_2$ to a concentration of 2000 U/mL. The bandages were removed from the freezer and placed on dry ice. Thrombin was sprayed at 37.5 $U/cm^2$. The bandages were returned to −80° C. for an additional 1 hour.

The bandages were placed on dry ice and received a second layer of fibrinogen (identical to the first layer). Half of the bandages were returned to −80° C. for 2 hours and the other half of the bandages were placed at −20° C. for 2 hours. Then, the bandages were placed in the freeze-dryer.

The bandages were subjectively assessed for resorbable material adherence and bandage appearance. Table 3 summarizes the experimental design.

TABLE 3

Various bandage configurations and formulations

| Bottom Layer | Second Layer | Third Layer | Fourth Layer | Freeze temp prior to placement into freeze-dryer | Bandage group |
|---|---|---|---|---|---|
| Fibrinogen 1 $mg/cm^2$ in 2% sucrose | VICRYL™ | Thrombin in 40 mM $CaCl_2$ | Fibrinogen 8 $mg/cm^2$ in 2% sucrose | −20° C. or −80° C. | 1 |
| Fibrinogen 1 $mg/cm^2$ in water | VICRYL™ | Thrombin in 40 mM $CaCl_2$ | Fibrinogen 8 $mg/cm^2$ in 2% sucrose | −20° C. or −80° C. | 2 |
| Fibrinogen 8 $mg/cm^2$ in 2% sucrose | VICRYL™ | Thrombin in 40 mM $CaCl_2$ | Fibrinogen 8 $mg/cm^2$ in 2% sucrose | −20° C. or −80° C. | 3 |
| Fibrinogen 8 $mg/cm^2$ in water | VICRYL™ | Thrombin in 40 mM $CaCl_2$ | Fibrinogen 8 $mg/cm^2$ in 2% sucrose | −20° C. or −80° C. | 4 |
| VICRYL™ | Fibrinogen 1 $mg/cm^2$ in 2% sucrose | Thrombin in 40 mM $CaCl_2$ | Fibrinogen 8 $mg/cm^2$ in 2% sucrose | −20° C. or −80° C. | 5 |
| VICRYL™ | Fibrinogen 1 $mg/cm^2$ in water | Thrombin in 40 mM $CaCl_2$ | Fibrinogen 8 $mg/cm^2$ in 2% sucrose | −20° C. or −80° C. | 6 |
| VICRYL™ | Fibrinogen 8 $mg/cm^2$ in 2% sucrose | Thrombin in 40 mM $CaCl_2$ | Fibrinogen 8 $mg/cm^2$ in 2% sucrose | −20° C. or −80° C. | 7 |
| VICRYL™ | Fibrinogen 8 $mg/cm^2$ in water | Thrombin in 40 mM $CaCl_2$ | Fibrinogen 8 $mg/cm^2$ in 2% sucrose | −20° C. or −80° C. | 8 |

RESULTS: The results from table 3 showed that the best bandage was. This was true for bandages frozen at both −20° C. or −80° C.

C. Example III

This bandage configuration had VICRYL™ and thrombin "layered" in between two layers of fibrinogen. The first layer of fibrinogen was solubilized in either 2% sucrose or water. The bandages were frozen at −20° C. or −80° C. prior to placement into the freeze-dryer. The experimental design is outlined in Table 4. The bandages were subjectively observed for physical appearance after freeze-drying and handling characteristics after hydration.

TABLE 4

"Layered" bandage configuration

| Bottom Layer | Second Layer | Third Layer | Fourth Layer | Fifth Layer | Freeze temp prior to placement into freeze-dryer | Group |
|---|---|---|---|---|---|---|
| 2% Sucrose | Fibrinogen 1 mg/cm² in 2% sucrose | VI-CRYL ™ | Thrombin in 40 mM CaCl₂ | Fibrinogen 8 mg/cm² in 2% sucrose | −20° C. or −80° C. | 1 |
| 2% Sucrose | Fibrinogen 1 mg/cm² in water | VI-CRYL ™ | Thrombin in 40 mM CaCl₂ | Fibrinogen 8 mg/cm² in 2% sucrose | −20° C. or −80° C. | 2 |
| 2% Sucrose | Fibrinogen 8 mg/cm² in 2% sucrose | VI-CRYL ™ | Thrombin in 40 mM CaCl₂ | Fibrinogen 8 mg/cm² in 2% sucrose | −20° C. or −80° C. | 3 |
| 2% Sucrose | Fibrinogen 8 mg/cm² in water | VI-CRYL ™ | Thrombin in 40 mM CaCl₂ | Fibrinogen 8 mg/cm² in 2% sucrose | −20° C. or −80° C. | 4 |

RESULTS: Two structures for layered bandage production; group 7 at −20° C. and −80° C. from table 3 and group 1 at −20° C. and −80° C. from table 4, were exhibited the best characteristics in terms of no separation of layers and attachment of resorbable material.

D. Example IV

Fibrinogen and thrombin were removed from the refrigerator and allowed to warm to room 25° C. for 2 hours. For groups 1+2 each vial of fibrinogen received 15.3 mL of 2% sucrose, final concentration of 26.2 mg/mL; bandages for group 3 had 21 mL of 2% sucrose to give a final concentration of 19.2 mg/mL,. The final amount of fibrinogen was 8 mg/cm² for all three groups.

DISPO™ molds (3.0×2.4 cm) were placed on a freezing tray on top of dry ice. 1 mL of 2% sucrose was added and allowed to freeze at −80° C. for 1 hour, once frozen VICRYL™ was placed on top and pressed into place. Groups 1+2 received 2.2 mL of fibrinogen, whereas group 3 received 1.5 mL of fibrinogen.

All bandages were allowed to freeze at −80° C. for 2 hours. Group 1 was kept at −80° C. until placed into the freeze dryer. Thrombin was solubilized with 0.5 mL of 40 mM CaCl₂ to a concentration of 2000 U/mL. Groups 2 & 3 were sprayed with thrombin, so that each bandage received 144 U/bandage while on dry ice. Once thrombin was applied the bandages were placed at −80° C. for 1 hour. Group 3 was removed from the freezer and placed on dry ice, and an additional 1.5 mL of fibrinogen at 19.2 mg/mL was added.

When finished all bandages were returned to −80° C. for another 2 hours. The bandages were then place into the freeze dryer, after 96 hours a sample of each group of bandages were removed and moisture content determined. Secondary drying was initiated for 24 hours. When the bandages were removed, moisture content was measured again.

RESULTS: As can be seen in table 5 the moisture content of the bandages decreases with secondary drying. All bandages looked identical and had the same texture.

TABLE 5

| Bandage Group | % Moisture | |
|---|---|---|
| | Pre-Secondary Drying | Post-Secondary Drying |
| Fibrinogen alone (1) | 4.2 | 3.8 |
| Fibrinogen/Thrombin (2) | 4.6 | 3.3 |
| Fibrinogen/Thrombin/Fibrinogen (3) | 4.3 | 3.9 |

E. Example V

Fibrinogen and thrombin were removed from the refrigerator and allowed to warm to room 25° C. for 2 hours. DISPO™ molds of size 3.0×2.4 cm were sprayed with 300 µL of 2% sucrose on dry ice, VICRYL™ was applied and pressed into place and the molds placed at −80° C. for 1 hour. Fibrinogen was solubilized with 11 mL of 2% sucrose, to a concentration of 36.4 mg/mL. Each bandage had a final fibrinogen amount of 15 mg/cm².

The molds received 1.5 mL of fibrinogen and then were frozen at −80° C. for 1 hour. Thrombin was solubilized with 0.5 mL of 40 mM CaCl₂ to a concentration of 2000 U/mL. All bandages were sprayed with thrombin, while on dry ice and received 37.5 U/cm².

The bandages were returned to −80° C. for an additional 1 hour. The bandages were placed on dry ice and received a second layer of fibrinogen, identical to the first layer. The bandages were again returned to −80° C. for 2 hours, until placed into the freeze dryer.

RESULTS: The bandages were removed from the freeze dryer and a sample of the 3.0×2.4 cm bandages was analyzed for moisture content. These bandages had a moisture content of 2.49%. The bandages were complete and had no separation of layers, and the VICRYL™ was well attached.

F. Example VI

Forty-four square petri dishes with a size of 10.1×10.1 cm, with a surface area of 103 cm² were placed on shelf trays and received 20 mL of 2% sucrose, which is equal to 194 µL/cm². Once the molds were filled they were placed at −80° C. for 2 hours until frozen, and then VICRYL™ was applied.

Fibrinogen and thrombin were removed from the refrigerator and allowed to warm to 25° C. for 2 hours. Each vial of fibrinogen was solubilized with 10 mL of 2% sucrose. The concentration of fibrinogen when reconstituted was 16 mg/mL. The molds received 25 mL of fibrinogen and where returned to −80° C. for 2 hours until frozen. Thrombin was solubilized with 0.5 mL of 40 mM CaCl₂ to a concentration of 2000 U/mL, and sprayed on top of the fibrinogen and returned to −80° C. for 1 hour. An additional 25 mL of fibrinogen was added and allowed to freeze at −80° C. for 2 hours.

The bandages were then freeze dried, upon completion the bandages were packaged and sent for in vivo testing, described supra.

G. Example VII

Fibrinogen and thrombin were removed from the refrigerator and allowed to warm to 25° C. for 2 hours. DISPO™ plastic molds (3.0 cm×2.4 cm) were placed on dry ice and sprayed with 300 µL of 2% sucrose. VICRYL™ or calcium alginate was applied and pressed into place. The molds were incubated at −80° C. for 1 hour.

The calcium alginate was used in two ways. In the first method, the calcium alginate was cut to the same size section as the VICRYL™ section. In the second method, the calcium alginate was also cut to the same size section as the VICRYL™ sections, but then it was shredded into fine pieces of material (Table 6).

Fibrinogen was solubilized with 11 mL of 2% sucrose to a concentration of 36.4 mg/mL. Each bandage had a final fibrinogen amount of 15 mg/cm$^2$. The molds received 1.55 mL of fibrinogen and then were frozen at −80° C. for 1 hour. Thrombin was solubilized with 0.5 mL of 40 mM CaCl$_2$ to a concentration of 2000 U/mL. The bandages were placed on dry ice and sprayed with thrombin to yield 37.5 U/cm$^2$.

The bandages were returned to −80° C. for 2 hours until they were placed into the freeze-dryer. After the bandages were freeze-dried, they were tested in the porcine arteriotomy bandage performance test.

TABLE 6

Bandage resorbable material combinations using Vicryl ™ and Calcium alginate

| Bandage | Vicryl | Calcium Alginate |
| --- | --- | --- |
| 1 | No | Whole |
| 2 | No | Shredded |
| 3 | Yes | Shredded |
| 4 | Yes | Whole |

Porcine Arteriotomy Bandage Performance Test

Obtain frozen porcine aorta and thaw. Aortas can be thawed overnight at 4° C., or individually wrapped in the water bath at 37° C. Dissect excess connective tissue from approximately first 11 cm of the aorta. Usually, the first 5–5.5 cm are free from collateral vessels. The next 5–5.5 cm should not have more than 1–2 collaterals. These can be easily sealed or patched with cyanoacrylate glue.

Cut the aorta into two 5.5 cm pieces. Invert aorta exposing the interior using a hemostat or blunt forceps. Wash both the interior and exterior of the vessel with 1–5 mL of PBS at 37° C. Stretch an O-ring over a 20cc syringe with an approximately 0.6 cm (0.25 in) hole drilled into one side. Using fingers or hemostats pull the vessel onto the syringe. Fit another O-ring of the same size onto the bottom.

Using curved hemostats, carefully secure both O-rings over the top of the vessel. The distance between both O-rings should be 3.5 cm. The artery should be snug fitting and held securely in place. Position the secured vessel such that the hole in the syringe lies in the middle of the distance between the O-rings.

Fill the syringe with PBS at 37° C. and place the screw through the outside of the syringe and into the plunger, so that the plunger is held in a stationary position. Wash the artery on the syringe with 1–2 ml of PBS at 37° C. Using a 16-gauge needle, make a hole in the center (approximately 1.75 cm from either O-ring) over the syringe hole. The 16-gauge needle should be replaced after every 12 uses.

Open the sealed bag containing the bandage and immediately place the bandage over the incision (approximately 0.5 cm from each O-ring, so as not to touch either O-ring). All bandages should be individually packaged prior to use.

Using a P-1000 PIPETMAN™ pipette, wet the bandage with PBS at 37° C. For 15 mg/cm$^2$ bandages use 800 μL, and for 8 mg/cm$^2$ bandages use 500 μL. Immediately place the syringe shield on top of the bandage, so as not to touch either O-ring. Press lightly to secure.

Place the syringe into the incubator at 37° C. using the holding box in order to keep the syringe and all its components stationary. Cover with the plastic cover, placing a 200 g weight securely over top. Assure even distribution of weight. Allow it to incubate for 5 minutes at 37° C.

Remove the syringe from the incubator. Carefully remove the shield covering the bandage. Attach the syringe to the tubing connected to a peristaltic pump. The tubing should be arranged so that it runs through the pump and is connected to a Y-junction on the opposite side. The Y-junction creates two outlets, allowing the PBS to be pumped into the syringe at one site as back pressure is being generated in the other. This back pressure is directly measured using an in-line pressure transducer-analyzer, and recorded using DMSI-200/1 software.

Pump the PBS at 37° C. into the syringe, and immediately start monitoring the pressure generated. Initiate a 30-second slow ramp (setting 4 at 1× speed for pump in E229, setting 7.5 at 1× speed for pump in E132), such that the initial flow rate is approximately 0.3 mL/min.

After the first 30 seconds, the flow rate is escalated to approximately 3 mL/min (10× speed, both settings). This should be done until a pressure of 200 mm Hg is obtained. Once 200 mm Hg is achieved, start the timer for 2 minutes.

Stop the pump once 200 mm Hg is obtained. Monitor the pressure generated. If pressure starts to drop, turn pump back on until adequate pressure is obtained. This may be done as often as necessary throughout the two-minute interval (under normal conditions, the pressure should be maintained between 200 and 215 mm Hg.). In addition, note any leakage and its location. If a leak occurs, note the maximum time and burst pressure at the moment of leakage. Judge bandage performance based on the following pass/fail criteria.

A bandage is considered passing if it maintains a fairly consistent pressure of 200 mm Hg for two minutes with absolutely no leakage. A bandage is also considered passing if it maintains a fairly consistent pressure of 200 mm Hg for two minutes with only minimal leakage (e.g., slow seeping or a leak that has resealed itself).

A bandage is considered failing if it cannot maintain adequate pressure due to severe leakage. This includes leakage caused by poor adhesion, as well as leakage due to manufacturing flaws.

RESULTS: The results of the experiment showed that bandages can be prepared using calcium alginate as a resorbable material or used as an additional component to the fibrinogen. There was no difference in the appearance of the bandages when removed from the freeze dryer. In addition, all groups of bandages when tested in the porcine arteriotomy assay held 200 mm Hg for 3 minutes.

H. Example VIII

Fibrinogen and thrombin were removed from the refrigerator and allowed to warm to 25° C. for 2 hours. DISPO™ plastic molds (2.4 cm×2.4 cm) were placed on dry ice and sprayed with 300 μl of 2% sucrose. Some of the molds had VICRYL™ applied and pressed into place and other molds had GELFOAM® (absorbable gelatin hemostat, Pharmacia) applied and pressed into place as a resorbable material.

Fibrinogen was solubilized with 11 mL of 2% sucrose to a concentration of 36.4 mg/ml, for the 15 mg/cm$^2$ bandages. Collagen Type 1 was solubilized with 95% ethanol to a concentration of 36.4 mg/mL.

In addition to the 15 mg/cm$^2$ bandages, 8 mg/cm$^2$ bandages were also prepared. The molds received 1.23 mL of fibrinogen or collagen and then were frozen at −80° C. for 1 hour. Thrombin was solubilized with 0.5 mL of 40 mM CaCl$_2$ to a concentration of 2000 U/mL. The bandages were placed on dry ice and sprayed with thrombin.

The bandages were returned to −80° C. for an additional hour. Then the bandages were placed on dry ice and received a second layer of fibrinogen (identical to the first layer). The bandages were returned to −80° C. for 2 hours until they were placed into the freeze-dryer.

Table 7 summarizes the experimental design. After freeze-drying, the bandages were subjectively assessed for their physical appearance.

TABLE 7

Formulation and configuration of bandages using different resorbable materials and different protein components

| 1st Layer | 2nd Layer | 3rd Layer | 4th Layer | 5th Layer |
|---|---|---|---|---|
| 2% sucrose | VICRYL ™ | Collagen I 15 mg/cm² | Thrombin | NA |
| 2% sucrose | VICRYL ™ | Collagen I 8 mg/cm² | Thrombin | NA |
| 2% sucrose | NA | Collagen I 15 mg/cm² | Thrombin | NA |
| 2% sucrose | NA | Collagen I 8 mg/cm² | Thrombin | NA |
| 2% sucrose | VICRYL ™ | Fibrinogen 15 mg/cm² | Thrombin | Fibrinogen 15 mg/cm² |
| 2% sucrose | VICRYL ™ | Fibrinogen 8 mg/cm² | Thrombin | Fibrinogen 8 mg/cm² |
| 2% sucrose | VICRYL ™ | Fibrinogen 7.5 mg/cm² + Collagen 7.5 mg/cm² | Thrombin | Fibrinogen 7.5 mg/cm² + Collagen 7.5 mg/cm² |
| 2% sucrose | VICRYL ™ | Fibrinogen 4 mg/cm² + Collagen 4 mg/cm² | Thrombin | Fibrinogen 4 mg/cm² + Collagen 4 mg/cm² |
| 2% sucrose | GELFOAM ® | Thrombin | NA | NA |
| 2% sucrose | GELFOAM ® | Fibrinogen 15 mg/cm² | | Fibrinogen 15 mg/cm² |
| 2% sucrose | GELFOAM ® | Fibrinogen 8 mg/cm² | | Fibrinogen 8 mg/cm² |

RESULTS: After freeze drying the bandages were evaluated for their physical appearance. All combinations manufactured produced satisfactory bandages. In that they were all intact and had no separation of layers.

I. Example IX

Fibrinogen and thrombin were removed from the refrigerator and allowed to warm to 25° C. for 2 hours. DISPO™ plastic molds (3.0 cm×2.4 cm) were placed on dry ice and sprayed with 300 μL of 2% sucrose. VICRYL™ was applied and pressed into place. The molds were incubated at −80° C. for 1 hour.

Fibrinogen was solubilized with 11 mL of 2% sucrose to a concentration of 36.4 mg/mL. Each bandage had a final fibrinogen amount of 15 mg/cm². Each group of bandages received their pre-determined designated amount of fibrinogen (as listed in Table 8). The bandages were then frozen at −80° C. for 1 hour.

TABLE 8

Bandage configurations with various percentages of fibrinogen

| 1st Layer: % Fibrinogen | Volume (ml) Fibrinogen | % Thrombin | 2nd Layer: % Fibrinogen | Volume (ml) Fibrinogen |
|---|---|---|---|---|
| 100 | 3.1 | 100 | 0 | 0 |
| 0 | 0 | 100 | 100 | 3.1 |

TABLE 8-continued

Bandage configurations with various percentages of fibrinogen

| 1st Layer: % Fibrinogen | Volume (ml) Fibrinogen | % Thrombin | 2nd Layer: % Fibrinogen | Volume (ml) Fibrinogen |
|---|---|---|---|---|
| 75 | 2.325 | 100 | 25 | 0.775 |
| 25 | 0.775 | 100 | 75 | 2.325 |
| 50 | 1.55 | 100 | 50 | 1.55 |

Thrombin was solubilized with 0.5 mL of 40 mM $CaCl_2$ to a concentration of 2000 U/mL. The bandages were placed on dry ice and sprayed with thrombin at 37.5 U/cm².

The bandages were returned to −80° C. for an additional hour. The bandages were placed on dry ice and received a second layer of fibrinogen (as listed in Table 8). The bandages were returned to −80° C. for 2 hours until they were placed into the freeze-dryer.

After freeze-drying, the bandages were tested in the porcine arteriotomy test. Bandages were tested on day 0 and two months post manufacturing after room temperature storage in foil bags.

TABLE 9

Porcine arteriotomy test results with various percentages of fibrinogen bandages

| % Fibrinogen (Bottom Layer) | % Thrombin (Middle Layer) | % Fibrinogen (Top Layer) | % Bandages that Passed Porcine Arteriotomy Test: | |
|---|---|---|---|---|
| | | | Time 0 | Time 2 months |
| 100 | 100 | 0 | 0 | 0 |
| 0 | 100 | 100 | 16.6 | 33.375 |
| 75 | 100 | 25 | 50 | 66.67 |
| 25 | 100 | 75 | 50 | 66.67 |
| 50 | 100 | 50 | 100 | 100 |

RESULTS: These results clearly show that the bandage produced with fibrinogen at 50% for the first layer and 50% for the second layer (fibrinogen 50/50 bandages) performs far superior to all other tested combinations of the bandages in this porcine arteriotomy model. Both at time 0 and 2 months, 100% of the fibrinogen 50/50 bandages passed the porcine arteriotomy test.

J. Example X

Fibrinogen and thrombin were removed from the refrigerator and allowed to warm to 25° C. for 2 hours. DISPO™ plastic molds (2.4 cm×2.4 cm) were placed on dry ice and sprayed with 300 μL of 2% sucrose. VICRYL™ was applied and pressed into place and the molds were placed at −80° C. for 1 hour.

Fibrinogen was solubilized with 11 mL of 2% sucrose to a concentration of 36.4 mg/mL. Each bandage had a final fibrinogen amount of 15 mg/cm². The molds received 1.23 mL of fibrinogen and then were frozen at −80° C. for 1 hour.

Thrombin was solubilized with 40 mM $CaCl_2$, 13 mM $CaCl_2$, or 4 mM $CaCl_2$. The bandages were placed on dry ice and sprayed with thrombin at either 37.5 U/cm², 12.5 U/cm², 4.2 U/cm², or 1.4 U/cm². The bandages were returned to −80° C. for an additional hour.

The bandages were placed on dry ice and received a second layer of fibrinogen (identical to the first layer). The bandages were returned to −80° C. for 2 hours until they were placed into the freeze-dryer. After the bandages were freeze-dried, they were evaluated for physical appearance and tested in the porcine arteriotomy test.

RESULTS: In this experiment, the bandages were produced using 40 mM, 13 mM, or 4 mM $CaCl_2$ to solubilize the thrombin and the bandages received thrombin at 37.5 $U/cm^2$, 12.5 $U/cm^2$, 4.2 $U/cm^2$, or 1.4 $U/cm^2$. Table 10 shows the experimental design and the results.

TABLE 10

Bandage (with variations in thrombin amount and $CaCl_2$ concentration) performance in the pig arteriotomy test

| Thrombin Units/$cm^2$ | $CaCl_2$ mM | Results % Bandages Separated Following Freeze Drying | % Bandages Pass Pig Arteriotomy |
|---|---|---|---|
| 1.4 | 4.4 | 100 | 0 |
| 4.2 | 4.4 | 100 | 0 |
| 12.5 | 4.4 | 100 | 0 |
| 37.5 | 4.4 | 0 | 0 |
| 1.4 | 13 | 87.5 | 50 |
| 4.2 | 13 | 25 | 0 |
| 12.5 | 13 | 12.5 | 75 |
| 37.5 | 13 | 0 | 100 |
| 1.4 | 40 | 87.5 | 0 |
| 4.2 | 40 | 12.5 | 83 |
| 12.5 | 40 | 12.5 | 100 |
| 37.5 | 40 | 0 | 100 |

The results from Table 10 show that the best combination for the bandage is 37.5 $U/cm^2$ of thrombin solubilized in either 13 mM or 40 mM $CaCl_2$. This combination is superior to all other combinations tested in both physical appearance and ability to pass the porcine arteriotomy test. These two combinations of the bandage exhibited no separation of the component layers after freeze-drying and 100% of the bandages passed the porcine arteriotomy test.

It should be noted that there were no adjustments made in the freeze-drying cycle when these bandages were manufactured so it is possible the cycle could be modified in such a way to consistently prepare bandages with lower thrombin and/or $CaCl_2$ amounts. However, a decrease in the amount of thrombin would prolong the amount of time needed for fibrin formation and may jeopardize the quality of the bandage, especially in case of trauma where the temperature of the body may be lower than normal thereby decreasing the bodies own clotting ability.

K. Example XI

Fibrinogen and thrombin were removed from the refrigerator and allowed to warm to 25° C. for 2 hours. DISPO™ plastic molds (2.4 cm×2.4 cm) were placed on dry ice and sprayed with 300 μL of 2% sucrose. VICRYL™ was applied and pressed into place. The molds were placed at −80° C. for 1 hour.

Fibrinogen was solubilized with 11 mL of 2% sucrose to a concentration of 36.4 mg/mL for 15 mg/$cm^2$, 21 mL of 2% sucrose to a concentration of 18.7 mg/mL for 8 mg/$cm^2$, 42.8 mL of 2% sucrose to a concentration of 9.35 mg/mL for 4 mg/$cm^2$, and 85.6 mL of 2% sucrose to a concentration of 4.68 mg/mL for 2 mg/$cm^2$. The molds received 1.23 mL of fibrinogen and then were frozen at −80° C. for 1 hour.

Thrombin was solubilized with 0.5 mL of 40 mM $CaCl_2$ to a concentration of 2000 U/mL. The bandages were placed on dry ice and sprayed with thrombin.

The bandages were returned to −80° C. for an additional hour. The bandages were placed on dry ice and received a second layer of fibrinogen (identical to the first layer).

The bandages were returned to −80° C. for 2 hours until they were placed into the freeze-dryer. After the bandages were freeze-dried, they were observed for their physical appearance and tested in the porcine arteriotomy test.

TABLE 11

% Bandages That Maintained 200 mm Hg for 3 minutes in Porcine Arteriotomy Assay

| Fibrinogen Concentration mg/$cm^2$ | % Bandages to Maintain 200 mm Hg |
|---|---|
| 15 | 100 |
| 8 | 50 |
| 4 | 37.5 |
| 2 | 18.75 |

L. Example XII

Fibrinogen and thrombin were removed from the refrigerator and allowed to warm to 25° C. for 2 hours. DISPO™ plastic molds (2.4 cm×2.4 cm) were placed on dry ice and sprayed with 300 μL of 2% sucrose.

Fibrinogen was solubilized with 11 mL of 2% sucrose to a concentration of 36.4 mg/mL. Each bandage had a final fibrinogen amount of 15 mg/$cm^2$. The molds received 1.23 mL of fibrinogen and then were frozen at −80° C. for 1 hour.

Thrombin was solubilized with 40 mM $CaCl_2$, the bandages were placed on dry ice and sprayed with thrombin at 37.5 $U/cm^2$. The bandages were returned to −80° C. for an additional hour.

The bandages were placed on dry ice and received a second layer of fibrinogen (identical to the first layer). VICRYL™ was applied and pressed into place and the molds were sprayed with 300 μL of 2% sucrose. The bandages were returned to −80° C. for 2 hours until they were placed into the freeze-dryer.

RESULTS: The bandages were evaluated for physical appearance when removed from the freeze dryer. Although the bandages layers were intact, the VICRYL™ was not attached to the bandage.

M. Example XIII

Fibrinogen was removed from the refrigerator and allowed to warm to 25° C. for 2 hours. Dispo plastic molds (2.4 cm×2.4 cm) were placed on dry ice and sprayed with 300 μL of 2% sucrose. Calcium alginate was applied and pressed into place.

Fibrinogen was solubilized with 11 mL of 2% sucrose to a concentration of 36.4 mg/mL. Each bandage had a final fibrinogen amount of 15 mg/$cm^2$. The molds received 2.4 mL of fibrinogen and then were frozen at −80° C. for 2 hours, then placed into the freeze dryer.

RESULTS: The bandages when removed from the freeze dryer were intact.

N. Example XIV

Fibrinogen and thrombin were removed from the refrigerator and allowed to warm to 25° C. for 2 hours. DISPO™ plastic molds (2.4 cm×2.4 cm) were placed on dry ice and sprayed with 300 μl of 2% sucrose. VICRYL™ was applied and pressed into place. Fibrinogen was solubilized with 11 mL of 2% sucrose to a concentration of 36.4 mg/mL; in addition, each vial received 0.2 grams of CHAPS (3-(3-cholamidopropyl) dimethylamino)-1-propanesulfonate).

Each bandage had a final fibrinogen amount of 15 mg/cm$^2$. The molds received 1.23 mL of fibrinogen/CHAPS and then were frozen at −80° C. for 1 hour.

Thrombin was solubilized with 40 mM CaCl$_2$; the bandages were placed on dry ice and sprayed with thrombin at 37.5 U/cm$^2$. The bandages were returned to −80° C. for an additional hour.

The bandages were placed on dry ice and received a second layer of fibrinogen/CHAPS (identical to the first layer). The bandages were returned to −80° C. for 2 hours until they were placed into the freeze-dryer.

RESULTS: The bandages when removed from the freeze dryer were intact and uniform in shape.

O. Example XV

The mean burst pressure of bandages incorporating different backing material and a fibrinogen concentration of 15 mg/cm$^2$ was determined.

| BACKING MATERIAL | FIBRINOGEN CONCEN- TRATION | MEAN BURST PRESSURE (mm Hg) | ADHERENCE TO BACKING MATERIAL |
|---|---|---|---|
| DEXON ™ #4 2000 micron | 8 mg/cm$^2$ | 15 | NO |
| DEXON ™ #4 230 micron | 8 mg/cm$^2$ | 250* | YES |
| DEXON ™ #8 100 micron | 8 mg/cm$^2$ | 181 | NO |
| VKML ™ KNITTED MESH | 8 mg/cm$^2$ | 250* | YES |
| VWML ™ WOVEN MESH | 8 mg/cm$^2$ | 210 | NO |

VKML ™ KNITTED MESH: VICRYL ™ knitted mesh (Ethicon)
VWML ™ WOVEN MESH: VICRYL ™ woven mesh (Ethicon)
* All of the bandages maintained mean burst pressure for the maximum test period of 3 minutes.

RESULTS: Maximum mean burst pressure and time was achieved with bandages at a concentration of 8 mg/cm$^2$. The mean burst pressure for VICRYL™ and DEXON™ meshes alone is zero.

P. Example XVI

Summary of In Vivo Data

Layered (Fibrinogen 50/50) Bandage Application Methods

Layered fibrinogen/thrombin/fibrinogen bandages at 15 mg/cm$^2$ fibrinogen were tested in the rat arterial hemorrhage model using two distinct application methods for the bandage: 1) the 500 g weight on a molded platform was used to apply pressure for fifteen minutes and with the variation that an additional one minute of pressure was applied if bleeding was noted or 2) finger pressure was applied for 7 minutes, and in the latter part of the study with the option to apply a second bandage with finger pressure for an additional 3 minutes if bleeding was noted after the first bandage. In all cases by either method, the bandage was applied to a dry field and the blood flow from the artery was used to soak the bandage.

Rat Hemorrhage Model

Animals: Model: Rat; Vendor: Harlan Sprague Dawley; Strain: Sprague Dawley; Color: White; Age: 120 days to 180 days; Sex: Male; Weight: 400 g to 500 g.

Anesthesia:
1) 1.1 g/Kg of 55% w/v Urethane (methyl carbamate) given IP
 a) Urethane supplied by: Sigma (lot 55H0368)
 b) Urethane prepared fresh daily by weighing out 2.0 g urethane into a sterile glass rubber-top tube (Becton Dickson, VACUTAINER™, 5 mL Draw Lot # 6A715 exp. December 1997). An equal weight/volume (2.0 cc) sterile water for injection (Abbott Laboratories, 10 ml Sterile Water for Injection, U.S.P., Lot 11–221-DK, Exp December 1, 1997) is added to produce a final solution volume of 3.6 mL (producing a solution of 55.56% urethane). This preparation procedure is performed in a biological safety cabinet (Forma Scientific, model 1168, serial no. 14088-43).
 c) The urethane injection is drawn into, and administered with, a 1 cc syringe(Becton Dickson, tuberculin 1 cc syringe, sterile Lot no. 3E345) with a 23 gauge. ¾ inch needle (Becton Dickson, PrecisionGlide needle, sterile Lot no. 4B047). The rat is weighed, manually restrained, and the urethane is injected intraperitoneally (IP) into the left caudal quadrant of the ventral abdomen. The volume injected ranges from 0.80 to 1.00 mL for rats weighing 400 to 500 g to deliver a dose of 1.1 g/Kg.
 d) Time clock started immediately after urethane injection recorded as T=0
2) 0.06 mg/Kg atropine and 0.15 mg/Kg buprenorphine given together IM.
 a) Atropine sulfate supplied by: Phoenix Pharmaceutical, Inc. (Lot# 5110547, Exp.11/96)
 b) Buprenorphine HCl (Buprenex) supplied by: Reckitt & Colman Pharmaceuticals (CN#3555, Exp. 1, Feb. '99)
 c) Atropine is drawn first into a 1 cc syringe (ibid) with a 26 gauge, ½ inch needle (Becton Dickson, Precision-Glide needle, sterile Lot no. 4B046), then the buprenorphine is drawn into the same syringe. The rat is given an intramuscular injection in the caudal thigh with the same syringe and needle when it has lost its righting reflex (2–3 minutes after the urethane injection). The volume injected is 0.04 to 0.05 mL of atropine, and 0.20 to 0.25 mL of buprenorphine, making a total volume of 0.24 to 0.30 mL for 400–500 g rats.
 d) Time of injection recorded to nearest minute Surgery:
1) Shave animal:
 a) Right axillary region for placement of thermoprobe
 b) Ventral Neck for right carotid artery cannulation
 c) Ventral abdominal midline for laparotomy
2) Thermoprobe placement:
 a) Stab incision right axilla with #15 or #17 scalpel blade
 b) Subcutaneous tissue undermined caudal to incision with Hartman mosquito forceps.
 c) Thermoprobe (TRACEABLE™, Certification of Calibration for Digital Thermometer, Model Number 15–784 078–39, Serial Number 566680) placed subcutaneously and temperature recorded
 d) Time of thermoprobe placement recorded to nearest minute
 e) Body temperature is maintained between 33 and 39° C. by the use of an electric heat support.
3) Carotid arterial cannulation/pressure transducer placement (under operating microscope):
 a) Ventral neck incised with from manubrium to mandibular symphysis—time recorded b) Cervical musculature bluntly dissected along fascial planes, exposing right carotid artery
c) Carotid artery bluntly dissected from surrounding tissue and distracted ventrally
d) Distal end of carotid exposure ligated with 4–0 silk, proximal end elevated with a length of 4–0 silk, and a third length of 4–0 silk placed under the artery midway between.
e) Beveled arteriotomy made with microvascular scissors and the transducer/catheter (Millar Mikro-Tip Catheter Pressure Transducer System, Size 2F, Model SPR-407) inserted into the artery 2–3 cm proximally, then ligated using the third length of silk with a quick release knot.
f) Instruments and elevating suture removed from the field, neck incision partially closed with a staple, and the rat situated in preparation for the laparotomy
g) Computerized data collection is begun—time recorded.*
h) At least five sets of data recorded at one minute intervals (mean arterialpressure, systolic and diastolic pressures, and heart rate readings), averaged over each minute.

4) Laparotomy (under operating microscope):
a) Ventral midline incision from xiphoid to pubis through skin and linea alba.
b) Abdominal incision retracted with Weitlaner Retractor (3×4 8" sharp), small intestine exteriorized to right side of animal and covered with warm saline moistened gauze, colonic mesentery bluntly dissected and colon displaced to the right.
c) Retroperitoneum bluntly dissected, exposing lumbar region of aorta/vena cava distal to the renal arteries. Adipose tissue cleaned away from vessel complex and surrounding muscle bed, creating a window approximately 2–3 cm diameter.
d) Diameter of aorta measured with micrometer calipers and documented.
e) Aorta clamped with Jacobson micro mosquito hemostatic forceps at cranial edge of window just distal to the renal arteries and clamped with Dieffenbach Micro Clamp at the caudal edge of window.
f) A 4 mm longitudinal incision is made using a microvascular scalpel and arteriotomy scissors on the ventral aspect of the aorta at the level of, or just distal to, the large lumbar veins. Incision measured with micrometer calipers and an ocular rule installed in the microscope eyepiece is utilized to guide the incision-making process.
g) Distal aortic clamp removed, proximal aortic clamp briefly released allowing approx. 0.5–1.0 mL of blood to fill the window, and to clear the artery of potential thromboses.
h) Bandage (either experimental fibrin sealant powder or IgG powder placebo control) placed onto the arteriotomy site, a custom made cylindrical molded platform (made with BONDO™ epoxy compound molded in a cylinder with one end against the internal side of a 400 g rat's back and gently sanded to a general conformation, weight=15.2 g) covered in thin plastic wrap placed over bandage, then a 500 g cylindrical brass weight (OHAUS) placed on platform and stabilized from tilting with a ring stand. This step done as quickly as possible (<1 min) and gentle manual pressure is applied throughout these manipulations.
i) Proximal aortic clamp is removed. If bleeding noted, a few seconds of manual pressure is applied and minor adjustments to position/angle of weight are made to achieve hemostasis. Often the weight tilts slightly forward less than 5 degrees. If hemostasis can not be achieved or excessive hemorrhage occurs (as indicated by MAP just prior to lifting the weight—see exclusion criteria below), then the animal must be excluded.
j) After 10 minutes of pressure, the weight is lifted and visible hemorrhage noted. If the MAP is <60 mmHg during the one minute period prior to lifting the weight (indicating excessive hemorrhage has occured prior to this point, or that the animal is responding aberrantly to the anesthesia), then the animal must be excluded. After one more minute, the molded platform is carefully removed, exposing the undisturbed bandage.
k) The animal is monitored until death occurs from exsanguination, or if hemostasis maintained, up to a maximum of 30 minutes. A positive result is hemostasis with the animal surviving the entire 30 minutes. A negative result is hemorrhage with death by exsanguination within the 30 min. test period. An intermediate result is survival through the 30 min. test period but the MAP not maintained above 50 mmHg.
l) If the rat survives the 30 min. test period, the carotid transducer is removed and exsanguination allowed to occur. After death, the blood is swabbed from the peritoneal cavity with reweighed gauze pads and the gauze reweighed to estimate blood loss. The bandage and arteriotomy site are inspected and the arterial incision is remeasured to confirm a length of 4 mm +/−0.5 mm.

Summary of Inclusionary/Exclusionary Criteria and Experimental Endpoints:
1) Inclusion criteria for rat selection:
a) HSD albino males
b) Weight between 400 and 500 g.
c) Age between 120 and 180 days
2) Inclusion criteria for procedural parameters:
a) MAP at least 80 mmHg average during the 5 minute period prior to laparotomy
b) HR between 300 and 500 bpm during the 5 minute period prior to laparotomy
c) MAP at least 60 mmHg average during the 1 minute period prior to lifting the weight
d) Length of aortic incision between 3.5 and 4.5 mm confirmed at end of procedure
3) Exclusion criteria for procedural parameters
a) Uncontrolled hemorrhage from a site other than the aortic arteriotomy
b) Death for some reason other than obvious hemorrhage
c) Uncorrectable surgical or procedural error
d) Any animals that do not meet the inclusion criteria above
4) Experimental endpoints
a) Primary endpoints
Hemostasis
Survival for 30 minutes after release of pressure on bandage
b) Secondary endpoints
MAP maintained above 50 mmHg for the entire 30 minutes of survival
c) Strong positive result
meets both primary and secondary endpoints
d) Intermediate positive result
Meets primary but not secondary endpoints e) Negative result Hemorrhage leading to death within 30 min.

RESULTS: This study showed that with the layered bandage applied by two different techniques yielded a success rate of exactly 50% by either method with an N of ten animals included per group.

With the weight and platform method, ten of nineteen animals were included in the study (5 pre-treatment and 4 post-treatment exclusions) with two post-treatment exclusions not surviving despite apparent hemostasis. Five of the ten included animals survived the 30 minute test period, while three of these survivors exhibited complete hemostasis.

With the application of a single bandage using finger pressure, ten of twelve animals were included (1 pre-treatment, and 1 post-treatment exclusion which died despite apparent hemostasis) with five of the ten subjects surviving thirty minutes. A second bandage was applied in an additional six animals, four of which were included (both pre-treatment exclusions), and two of the four included animals survived thirty minutes. Often, there was not enough time to apply a second bandage before too much blood had been lost. In nearly all cases of failure, the blood flow from the artery dissected the plane between the bandage and the tissue—in only one case was blood seen flowing through the bandage matrix. The adherence of the bandage to the tissues was good except where natural hematomas had formed under the bandage creating a pocket of weaker fibrin. In many cases, the bandage was not fully saturated by the blood.

Arterial Hemorrhage Model in the Rabbit

The rabbit aorta model has several advantages over the rat model: the artery can be isolated from the underlying tissue to provide direct access to the injury site, a plate can be placed under the aorta to provide a background for applying pressure, the artery is large enough to test various incision sizes and configurations, and the rabbit has a large enough blood volume to tolerate reasonable blood losses necessary to soak the bandage or apply multiple bandages. A disadvantage of the rabbit is lack of a good anesthetic regimen that can maintain high blood pressures—a problem that was addressed by the use of vasopressors.

New Zealand white male rabbits weighing 2.9–3.3 kg have been used in this study. Rabbits are premedicated with buprenorphine and glycopyrrholate, and anesthesia induced with ketamine and xylazine, administered IM. An endotracheal tube is placed via tracheotomy and mechanical ventilation assistance is provided. Anesthesia is maintained by isoflurane in oxygen. The animals' condition is monitored by electrocardiography and visual observation. A 22 gauge angiocath is inserted in the left medial ear vein and IV drip of Lactated Ringer's solution is administered at a surgical rate of 20 ml/Kg/hr. Bilateral vagotomy is performed in order to avoid vagally-mediated cardiovascular effects. A solid state pressure transducer is inserted in the right common carotid artery to monitor blood pressures and computer recording is initiated.

The abdominal aorta is exposed via a ventral midline laparotomy, and the aorta is carefully dissected away from the vena cava and surrounding tissues. Small branching arteries are ligated or cauterized, isolating a 6–8 cm length of artery. A plastic rectangular plate is inserted under exposed portion of the aorta. Blood flow is occluded distally and proximally with Jacobsen hemostatic forceps. A 5 mm longitudinal incision is made with a microblade and fine scissors.

A 15 mg/cm$^2$ (2.4×2.4 cm.) fibrinogen/thrombin/fibrinogen bandage applied to an injured site by a variety of techniques being tested in the initial studies. A soft gel-filled plastic pad is applied over the bandage and 500 gram weight is placed on the top of the pad. The clamps are removed and the weight is used to apply pressure for ten minutes (this time period will vary in subsequent studies). After the specified time, the weight and gel-pad are removed. Shortly afterward the plastic plate is carefully removed from under the bandage. The observation period is thirty minutes after removal of the weight. Five minutes into the observation period, a phenylephrine IV drip is initiated to boost the animal's mean arterial pressure above 100 mmHg and is continued at increasing rates until the end of the observation period or death of the animal from exsanguination.

The preliminary model development study involves at least the following five groups: 1) dry bandage placed under the aorta, soaked with 2–3 mL of saline, and folded around the injury site before the weight is applied; 2) as in group 1, but the bandage is soaked with blood freshly drawn from the animal; 3) dry bandage placed flat over the incision and soaked with saline just before pressure is applied; 4) dry bandage placed flat over the incision and allowed to soak with blood flowing from the artery; and 5) a placebo bandage applied by the most effective technique above. In the fourth group, the clamps are released immediately after the bandage is in place to allow blood flow, and the weight is applied as soon as blood flow is visibly soaking the bandage.

RESULTS: Hemostasis occurs in 50% of animals when the bandage is hydrated by blood flowing from the wound itself, but hemostasis is achieved in 100% of animals under controlled conditions where saline was used to wet the bandage. The reason for the differences seen when blood flowing from the artery was used to soak the bandage are unclear.

Prostatectomy Hemorrhage Model in the Dog

Fibrinogen/thrombin/fibrinogen bandages were prepared for a canine prostatectomy study. The fibrinogen and thrombin were removed from the refrigerator and allowed to warm to 25° C. for 2 hours. DISPO™ plastic molds (3.0 cm×2.4 cm and 3.7 cm×2.4 cm) were placed on dry ice and sprayed with 300 μL of 2% sucrose. VICRYL™ was applied to the molds and pressed into place. The molds were incubated at −80° C. for 1 hour.

Fibrinogen was solubilized with 11 mL of 2% sucrose to a concentration of 36.4 mg/mL. Each bandage had a final fibrinogen amount of 15 mg/cm$^2$. The 3.0×2.4 cm molds received 1.5 mL of fibrinogen; whereas, the 3.7×2.4 cm molds received 1.75 mL of fibrinogen. The bandages were frozen at −80° C. for 1 hour.

Thrombin was solubilized with 0.5 mL of 40 mM CaCl$_2$ to a concentration of 2000 U/mL. All of the bandages were placed on dry ice and sprayed with thrombin. Each bandage received thrombin at 37.5 U/cm$^2$. The bandages were returned to −80° C. for an additional 1 hour.

The bandages were placed on dry ice and received a second layer of fibrinogen (identical to the first layer). The bandages were returned to −80° C. for 2 hours and then they were placed into the freeze-dryer.

In this prostatectomy model, a midline abdominal incision is made and a splenectomy performed. The prostate is bluntly dissected free and the urethra is isolated just distal to the prostate. The urethra is incised anteriorly, the foley catheter is drawn upward into the wound, and the posterior urethra transected. The vascular pedicles to the prostate are transected sharply. Bleeding is controlled with lap sponges and manual pressure while the bladder neck is dissected free from the prostate. The prostate is delivered from the operative field.

At this point, if there is bleeding, vessels are isolated and ligated. The time to achieve hemostasis is measured from the time the prostate is delivered until there is no further bleeding. Acute blood loss is calculated by subtracting the weight of the lap sponges preoperatively from the post operative weight.

The study was comprised of four experimental treatment groups: control, fibrin sealant bandage, placebo bandage, and liquid fibrin sealant. The control is the application of lap sponges and manual pressure. The experimental group is the application of the fibrin sealant bandage over the bleeding area prior to placing the lap sponges and manual pressure. Additionally, the anastomosis is wrapped with two (1×3 cm) bandages. The placebo bandage is a visually identical layered lyophilized IgG protein preparation which is treated the same as the experimental fibrin sealant bandage group. The liquid fibrin sealant is fibrinogen, Factor XIII, and thrombin solutions that are mixed and applied to bleeding surfaces prior to pressure application. Additionally, 6 ml of this sealant is applied to the anastomosis.

RESULTS: The preliminary results from this canine prostatectomy study indicate that the fibrin sealant bandage successfully controls bleeding in this model (Table 12).

TABLE 12

Efficacy of fibrin sealant bandage in canine prostatectomy study

|  | Control | Placebo bandage | Fibrin sealant bandage | Liquid fibrin sealant |
|---|---|---|---|---|
| Number of animals | 4 | 5 | 3 | 3 |
| Blood loss (mL) | 240 ± 22 | 249 ± 22 | 114 ± 9 | 238 ± 32 |
| Ligated vessels | 4/4 | 5/5 | 0/3 | 3/3 |

In the table, "ligated vessels" refers to the number of animals that needed vessels ligated in order to stop bleeding after the prostate is removed. Only the dogs that were treated with the fibrin sealant bandage did not need vessels ligated.

Liver Injury Hemorrhage Model in the Pig

Layered bandages were prepared for a swine liver injury model. Fibrinogen and thrombin were removed from the refrigerator and allowed to warm to 25° C. for 2 hours. Forty-four square petri dish molds (10.1 cm×10.1 cm), with a surface area of 103 cm$^2$, were placed on shelf trays from the freeze-dryer. Each petri dish received 20 mL of 2% sucrose to yield 194 µL/cm$^2$.

After adding the 2% sucrose, the molds were placed at −80° C. for 2 hours until frozen. VICRYL™ was applied and pressed into place. The molds were returned to −80° C. for 1 hour.

Each vial of fibrinogen was solubilized with 10 mL, of 2% sucrose to a final concentration of 16 mg/mL. The molds received 25 mL of fibrinogen and were returned to −80° C. for 2 hours until frozen.

Thrombin was solubilized with 0.5 mL of 40 mM CaCl$_2$ to a concentration of 2000 U/mL. The bandages were placed on dry ice, sprayed with thrombin and incubated at −80° C. for 1 hour.

An additional 25 mL of fibrinogen was added on top of the thrombin. The bandages incubated at −80° C. for 2 hours until they were placed into the freeze-dryer.

After freeze-drying, the bandages were packaged and sent testing in the swine liver injury study.

Studies were conducted to test the efficacy of the fibrin sealant bandage and to determine the effect of fibrinogen dose on blood loss. Under general anesthesia, each pig underwent laparotomy and splenectomy. Following a 15 minute period, a Grade IV liver injury was induced using a specially designed instrument. After 30 seconds, the bandages were applied to the injury. Resuscitation with lactated Ringer's solution was simultaneously initiated and the animals were resuscitated to pre-injury mean arterial pressure. The abdominal incision was then closed and the pig was monitored for 60 minutes. The animals were euthanized at 60 minutes. Blood samples were collected at pre-injury and at 30 and 60 minutes post-injury. CBC, fibrinogen, PT, and PTT were determined at each time point. At 60 minutes, the total fluid use and the volume of blood present in the abdominal cavity (total blood loss) were determined. Additionally, the liver was excised and the injury was scored to confirm a Grade IV injury.

RESULTS: The study of a porcine liver injury model to test the efficacy of the fibrin sealant (FS) bandage to prevent hemorrhage has shown that the FS bandage is far superior to standard treatment using fluid resuscitation and gauze application. The study consisted of four groups: (1) no treatment, (2) IgG bandage (placebo), (3) gauze packing, and (4) fibrin sealant bandage. All animals in each group received fluid resuscitation to compensate for the shed blood. The animals were monitored for 60 minutes.

Group 1 (no treatment group) lost 6,025±1,020 cc of blood per animal and the animals died. Group 2 (placebo bandage) lost 4,222±1,554 cc of blood per animal and the animals died. Group 3 (gauze application group) lost 1,104±263 cc of blood per animal. Group 4 (fibrin sealant bandage group) lost 544±104 cc of blood per animal.

Similar results were observed when pigs were made coagulopathic by both dilution and hypothermia, except that under these more stringent conditions, the animals treated with guaze packing exsanguinated, while those treated with the fibrinogen/thrombin/fibrinogen bandage survived.

Initial Bandage Fibrinogen Dosage Study

The blood loss in the control group was 2819±629 mL (mean±SEM) which was significantly greater than any of the treatment groups (p<0.05).

Blood loss in the fibrin sealant bandage treatment groups did not differ significantly from each other. The volumes were 588±629 mL, 632±703 mL, and 758±629 mL in the 15, 8, and 4 mg fibrinogen/cm$^2$ groups, respectively.

The total fluid resuscitation volume was 2757±565 mL, 1448±505 mL, 1775±505 mL. and 2208±565 mL for the control 15 mg, 8 mg, and 4 mg fibrinogen/cm$^2$ groups, respectively. The fibrinogen and all CBC components decreased as the blood loss increased. PT and PTT increased.

Some of the clots from the fibrin sealant bandages used in the pigs were examined: 3/3 control bandages did not adhere, 3/3 in the 15 mg/cm$^2$ bandage group adhered well, 3/3 in the 8 mg/cm$^2$ bandage group adhered, and 3/3 in the 4 mg/cm$^2$ bandage group adhered slightly. One pig died prior to 60 minutes in each of the control, 4 mg, and 8 mg treatment groups. All of the animals survived to 60 minutes in the 15 mg group. This study confirms the previous finding that the fibrin sealant bandage decreases blood loss following Grade V liver injury in swine.

The data suggest that fibrinogen levels from 4 mg to 15 mg/cm$^2$ are effective for hemorrhage control. Based on assessments of the clot quality, it appears that fibrinogen dose is related to quality. The higher dose is associated with more firm and tightly adhered clots. While lower fibrinogen doses are effective for hemorrhage control during the initial 60 minutes, longer term survival will likely depend on clot quality. Future survival studies will focus on determining the amount of fibrinogen that produces both short term (60 min) and longer term hemostasis and survival.

What is claimed is:

1. A hemostatic sandwich bandage for treating wounded tissue in a patient which comprises:
   (i) a first fibrinogen layer;
   (ii) a thrombin layer adjacent to said first fibrinogen layer; and
   (iii) a second fibrinogen layer adjacent to said thrombin layer.

2. A hemostatic sandwich bandage for treating wounded tissue in a patient which comprises:
   (i) a resorbable material layer;
   (ii) a first fibrinogen layer adjacent to said resorbable material layer;
   (iii) a thrombin layer adjacent to said first fibrinogen layer; and
   (iv) a second fibrinogen layer adjacent to said thrombin layer.

3. A hemostatic sandwich bandage for treating wounded tissue in a patient which comprises:
   (i) a first fibrinogen layer;
   (ii) a resorbable material layer adjacent to said first fibrinogen layer;
   (iii) a thrombin layer adjacent to said resorbable material layer; and
   (iv) a second fibrinogen layer adjacent to said thrombin layer.

4. The hemostatic bandage according to any one of claims 1 to 3, further comprising a backing material.

5. The hemostatic sandwich bandage of claim 2 or 3, wherein said resorbable material layer comprises a material selected from the group consisting of glycolic acid polymers, lactic acid polymers and glycolic acid/lactic acid co-polymers.

6. The hemostatic sandwich bandage of claim 2 or 3, wherein one or more of said layers contains a solubilizing agent.

7. The hemostatic sandwich bandage according to any one of claims 1 to 3, wherein one or more of said layers contains a filler.

8. The hemostatic sandwich bandage according to any one of claims 1 to 3, wherein one or more of said layers contains a binding agent.

9. A method of treating wounded tissue, which comprises applying to said wounded tissue a hemostatic sandwich bandage according to any one of claims 1 to 3.

* * * * *

UNITED STATES PATENT AND TRADEMARK OFFICE
CERTIFICATE OF CORRECTION

PATENT NO.   : 6,762,336 B1
DATED        : July 13, 2004
INVENTOR(S)  : Martin J. MacPhee It is certified that error appears in the above-identified patent and that said Letters Patent is hereby corrected as shown below:

Title page,
Item [75], Inventors, replace "Montgomery Village, CA" with -- Montgomery Village, MD --; and replace "William H. Drohan" with -- William N. Drohan --.

Signed and Sealed this

Twenty-third Day of November, 2004

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,762,336 B1 | Page 1 of 1 |
| APPLICATION NO. | : 09/890795 | |
| DATED | : July 13, 2004 | |
| INVENTOR(S) | : Martin J. MacPhee | |

It is certified that error appears in the above-identified patent and that said Letters Patent is hereby corrected as shown below:

On the Title Page Item (75) under the inventors, replace "Montgomery Village, CA" with --Montgomery Village, MD--.

Signed and Sealed this
Nineteenth Day of April, 2016

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 6,762,336 B1 | Page 1 of 1 |
| APPLICATION NO. | : 09/890795 | |
| DATED | : July 13, 2004 | |
| INVENTOR(S) | : MacPhee et al. | |

It is certified that error appears in the above-identified patent and that said Letters Patent is hereby corrected as shown below:

At column 1, line 5, please insert the following heading and text:

--STATEMENT REGARDING FEDERALLY SPONSORED RESEARCH OR DEVELOPMENT

This invention was made with government support under Grant No. DAMD 17-95-1-5059 awarded by the U.S. Army Medical Research and Materiel Command. The government has certain rights in the invention.--

Signed and Sealed this
Twenty-eighth Day of June, 2016

Michelle K. Lee
*Director of the United States Patent and Trademark Office*